(12) United States Patent
Koshi et al.

(10) Patent No.: US 9,980,913 B2
(45) Date of Patent: May 29, 2018

(54) IMMUNOGENIC COMPOSITION

(71) Applicant: Toray Industries, Inc., Tokyo (JP)

(72) Inventors: Yoichiro Koshi, Kamakura (JP); Reiji Nishio, Kamakura (JP); Yoshinori Kakizawa, Kamakura (JP)

(73) Assignee: Toray Industries, Inc. (JP)

( * ) Notice: Subject to any disclaimer, the term of this patent is extended or adjusted under 35 U.S.C. 154(b) by 0 days. days.

(21) Appl. No.: 14/887,722

(22) Filed: Oct. 20, 2015

(65) Prior Publication Data

US 2016/0038421 A1 Feb. 11, 2016

Related U.S. Application Data

(62) Division of application No. 13/819,015, filed as application No. PCT/JP2011/069122 on Aug. 25, 2011.

(30) Foreign Application Priority Data

Aug. 26, 2010 (JP) .................................. 2010-189307

(51) Int. Cl.
| | |
|---|---|
| *A61K 9/16* | (2006.01) |
| *A61K 39/39* | (2006.01) |
| *A61K 39/00* | (2006.01) |

(52) U.S. Cl.
CPC .......... *A61K 9/1682* (2013.01); *A61K 9/1623* (2013.01); *A61K 9/1641* (2013.01); *A61K 9/1647* (2013.01); *A61K 9/1652* (2013.01); *A61K 39/0011* (2013.01); *A61K 39/39* (2013.01); *A61K 2039/55583* (2013.01); *A61K 2039/6087* (2013.01); *A61K 2039/6093* (2013.01)

(58) Field of Classification Search
None
See application file for complete search history.

(56) References Cited

U.S. PATENT DOCUMENTS

| | | |
|---|---|---|
| 2005/0191358 A1 | 9/2005 | O'Hagan et al. |
| 2008/0145432 A1 | 6/2008 | Kakizawa et al. |
| 2008/0199491 A1 | 8/2008 | Brandon et al. |
| 2010/0285135 A1 | 11/2010 | Wendorf et al. |
| 2011/0003007 A1 | 1/2011 | Kakizawa et al. |
| 2011/0300223 A1 | 12/2011 | Nishio et al. |

FOREIGN PATENT DOCUMENTS

| | | |
|---|---|---|
| JP | 2001-503254 A | 3/2001 |
| JP | 2008-502605 A | 1/2008 |
| JP | 2008-088158 A | 4/2008 |
| WO | 2006/095668 A1 | 9/2006 |
| WO | 2007/100699 A2 | 9/2007 |
| WO | 2009/095226 A2 | 8/2009 |
| WO | 2009-104706 A1 | 8/2009 |
| WO | 2009/111337 A1 | 9/2009 |
| WO | 2010/098432 A1 | 9/2010 |

OTHER PUBLICATIONS

Yang et al., "Morphology, drug distribution, and in vitro release profiles of biodegradable polymeric microspheres containing protein fabricated by double-emulsion solvent extraction/evaporation method", 2001, vol. 22., pp. 231-241.*
H. Rafati et al., "The immune response to a model antigen associated with PLG microparticles prepared using different surfactants," Vaccine, vol. 15, No. 17/18, 1997, pp. 1888-1897.
Li Youxin et al., "Biodegradable brush-like graft polymers from poly(D,L-lactide) or poly(D,L-lactide-coglycolide) and charge-modified, hydrophilic dextrans as backbone-in-vitro degradation and controlled releases of hydrophilic macromolecules," Polymer, vol. 39, No. 14, 1998, pp. 3087-3097.
Wenlei Jiang et al., "Biodegradable poly(lactic-co-glycolic acid) microparticles for injectable delivery of vaccine antigens," Advanced Drug Delivery Reviews, vol. 57, Issue 3, Jan. 10, 2005, pp. 391-410.
S.S. Moni et al., "Immune Augmentation of Injectable PLGA-Dextran (PLDEX) a Double Polymeric Microspheres as an Adjuvant for Hepatitis B Vaccine," World Journal of Vaccines, vol. 1, 2011, pp. 104-108.
European Supplementary Search Report dated May 8, 2014 for corresponding European Patent Application No. 11 81 9971.
David H. Donabedian et al., "Acylation of Pullulan by Ring-Opening of Lactones," Macromolecules, vol. 31, Issue 4, 1998, pp. 1032-1039 (Abstract).
S.J. de Jong et al., "Novel Self-assembled Hydrogels by Stereocomplex Formation in Aqueous Solution of Enantiomeric Lactic Acid Oligomers Grafted to Dextran," Macromolecules, vol. 33, Issue 10, 2000, pp. 3680-3686 (Abstract).
Ya-Ping Li et al., "PEGylated PLGA nanoparticles as protein carriers: synthesis, preparation and biodistribution in rats," Journal of Controlled Release, vol. 71, Issue 2, 2001, pp. 203-211 (Abstract).
Tatsuro Ouchi et al., "Modification of polylactide upon physical properties by solution-cast blends from polylactide and polylactide-grafted dextran," Polymer, vol. 44, Issue 14, 2003, pp. 3927-3933 (Abstract).

* cited by examiner

*Primary Examiner* — Robert A Wax
*Assistant Examiner* — Randeep Singh
(74) *Attorney, Agent, or Firm* — DLA Piper LLP (US)

(57) ABSTRACT

A process of producing an immunogenic particle includes mixing an aqueous solvent A wherein an antigen(s) is/are dissolved and a water-immiscible organic solvent B wherein an amphiphilic polymer(s) whose hydrophobic segment(s) is/are poly(hydroxy acid) is/are dissolved, to form a reversed-phase emulsion; and removing the solvent from the reversed-phase emulsion to obtain an antigen-adjuvant microparticle complex, wherein the aqueous solvent A and/or the water-immiscible organic solvent B contains a surfactant.

18 Claims, 3 Drawing Sheets

IMMUNOGENIC COMPOSITION

RELATED APPLICATIONS

This application is a divisional of U.S. Ser. No. 13/819,015, filed Feb. 26, 2013, which is a § 371 of International Application No. PCT/JP2011/069122, with an international filing date of Aug. 25, 2011 (WO 2012/026508 A1, published Mar. 1, 2012), which is based on Japanese Patent Application No. 2010-189307, filed Aug. 26, 2010.

TECHNICAL FIELD

This disclosure relates to an immunogenic composition comprising as an effective ingredient an immunogenic microparticle, which immunogenic microparticle comprises: an antigen-adjuvant microparticle complex wherein an antigen(s) is/are encapsulated in an adjuvant microparticle composed of an amphiphilic polymer(s); and a surfactant.

BACKGROUND

To enhance the immune-activating capacity of an antigen, an adjuvant is used together with the antigen. Although complete Freund's adjuvant (CFA) is known to have an excellent effect as an adjuvant, CFA is composed of killed bacteria and an oil emulsion and, hence, has strong side effects such as strong inflammatory reaction and formation of ulcerative swelling (granuloma) at the administration site. Therefore, use of CFA for humans is not permitted in view of safety. Accordingly, adjuvants whose administration to humans is permitted are limited.

Examples of adjuvants whose administration to humans is permitted include aluminum hydroxide adjuvants, but their immune-activating capacities are not necessarily sufficient and, hence, they need to be repeatedly administered to achieve acquisition of immunity. Therefore, development of an immunogenic composition using an efficient and strong adjuvant, which composition can be used for humans, has been demanded.

To develop a novel adjuvant aiming to attain a high immune-activating capacity, a method wherein an antigen is encapsulated in a microparticle has been attempted. It has been reported that administration of a microparticulated antigen enhances immunological reactions such as antibody production compared to administration of an antigen alone, but the effect of its administration is not necessarily high, and only an effect at almost the same level as in the above-mentioned aluminum hydroxide adjuvant has been reported. This is considered to be due to the difficulty in efficiently encapsulating hydrophilic antigen molecules such as proteins in microparticles studied so far such as microparticles composed of hydrophobic polylactic acid-polyglycolic acid copolymers while maintaining the structures of the antigen molecules (Advanced Drug Delivery Reviews, 2005, Vol. 57, pp. 391-410).

In recent years, a novel microparticle technology has been reported (WO 2006/095668 and JP 2008-088158 A), which technology uses an amphiphilic polymer and enables highly efficient encapsulation of a high molecular weight protein. Although this novel microparticle has been studied for its sustained-release performance for drugs, its adjuvant function in cases of encapsulation of an antigen therein has not been studied at all. Further, in terms of the mechanism by which a microparticle containing an antigen functions as an adjuvant, it is thought that the function for sustained release of the antigen molecule as well as the mechanism by which the microparticle containing an antigen is incorporated in its entirety into an immunocyte and releases the antigen in the cell are important, and that the function of drug release from the particle and the performance as an adjuvant are not necessarily correlated with each other. Therefore, it is difficult to infer the adjuvant function based on the sustained-release performance of the particle, and an effective adjuvant having a much better performance than aluminum adjuvants has not been realized so far by conventional technologies using microparticles in spite of the demand for its development.

There is, therefore, a need to provide an immunogenic composition which shows a high immune-activating capacity even with a small antigen amount and/or a small number of doses.

SUMMARY

We studied a method by which a high level of immune activation can be induced using a small amount of antigen and with a small number of doses thereof and, as a result, discovered that an immunogenic composition comprising as effective ingredients: an immunogenic microparticle composed of an antigen-adjuvant microparticle complex wherein an antigen(s) is/are encapsulated in an adjuvant microparticle; and a surfactant; has a high immune-activating capacity in vivo.

We thus provide:

(1) An immunogenic composition comprising, as effective ingredients: an immunogenic microparticle composed of an antigen-adjuvant microparticle complex wherein an antigen(s) is/are encapsulated in an adjuvant microparticle composed of an amphiphilic polymer(s) whose hydrophobic segment(s) is/are poly(hydroxy acid); and a surfactant; the surfactant being encapsulated in the immunogenic microparticle.

(2) The immunogenic composition according to (1), wherein the immunogenic microparticle is a particle composed of the antigen-adjuvant microparticle complex associated together.

(3) The immunogenic composition according to (1) or (2), wherein the surfactant comprises a fatty acid ester structure.

(4) The immunogenic composition according to any one of (1) to (3), wherein the adjuvant microparticle has, in the inner portion thereof, a hydrophilic portion(s) composed of a hydrophilic segment(s) of the amphiphilic polymer(s), and has an outer layer composed of a hydrophobic portion(s) composed of a hydrophobic segment(s) of the amphiphilic polymer(s).

(5) The immunogenic composition according to any one of (1) to (4), wherein the hydrophilic segment of the amphiphilic polymer is a polysaccharide.

(6) The immunogenic composition according to any one of (1) to (5), wherein the amphiphilic polymer is a graft amphiphilic polymer composed of a polysaccharide backbone and a poly(hydroxy acid) graft chain(s).

(7) The immunogenic composition according to (5) or (6), wherein the polysaccharide is dextran.

(8) The immunogenic composition according to any one of (1) to (7), wherein the poly(hydroxy acid) is poly(lactic-co-glycolic acid).

(9) The immunogenic composition according to any one of (1) to (8), wherein the surfactant further comprises a monosaccharide and/or polyethylene glycol structure(s).

(10) The immunogenic composition according to any one of (1) to (9), wherein the surfactant is one or more selected from the group consisting of polysorbate 80, polysorbate 20, sorbitan monooleate, sorbitan trioleate and polyoxyethylene hydrogenated castor oil.

(11) An immunogenic composition comprising as an effective ingredient an immunogenic microparticle obtained by the steps of:
dissolving a surfactant(s) in an aqueous solvent A wherein an antigen(s) is/are dissolved or in a water-immiscible organic solvent B wherein an amphiphilic polymer(s) whose hydrophobic segment(s) is/are poly(hydroxy acid) is/are dissolved, and mixing the resulting mixture to form a reversed-phase emulsion; and
removing the solvent from the reversed-phase emulsion.

(12) A process of producing a particle composed of an antigen-adjuvant microparticle complex associated together, the process comprising the steps of:
mixing an aqueous solvent A wherein an antigen(s) is/are dissolved and a water-immiscible organic solvent B wherein an amphiphilic polymer(s) whose hydrophobic segment(s) is/are poly(hydroxy acid) is/are dissolved, to form a reversed-phase emulsion;
removing the solvent from the reversed-phase emulsion to obtain an antigen-adjuvant microparticle complex; and
introducing an antigen-adjuvant microparticle complex dispersion C to a liquid phase D wherein a surface modifier is dissolved, followed by removing the dispersion medium;
wherein a surfactant(s) is/are dissolved in the aqueous solvent A, water-immiscible organic solvent B and/or dispersion C.

An immunogenic composition with which stronger immune activation than before is possible in vivo is provided.

DETAILED DESCRIPTION

Figure 1:
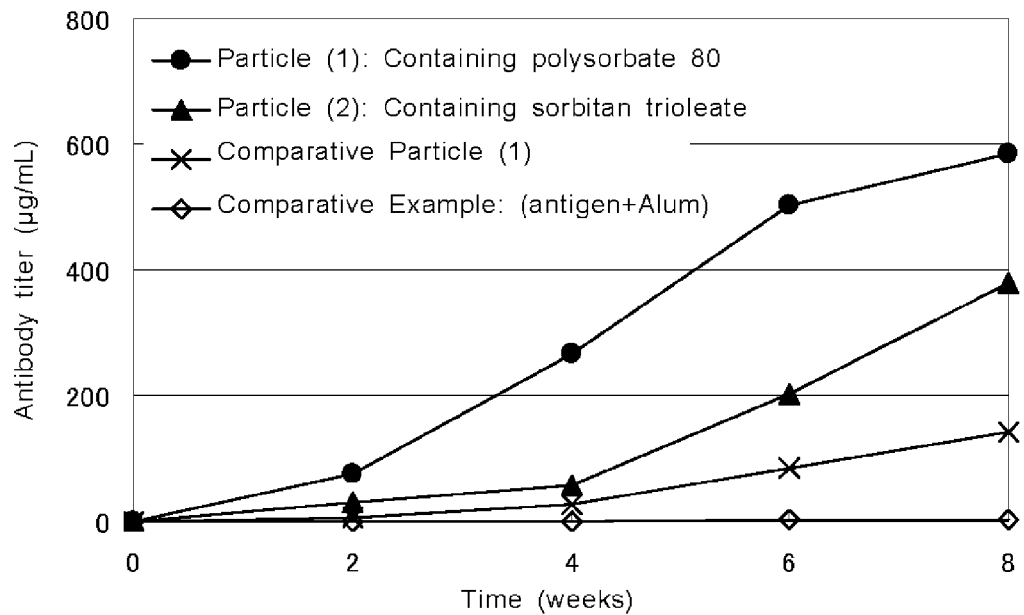
FIG. 1 shows immunological evaluation 1 of CEA-containing immunogenic microparticles.

Our compositions and methods relate to an immunogenic composition comprising as effective ingredients: an immunogenic microparticle composed of an antigen-adjuvant microparticle complex wherein an antigen(s) is/are encapsulated in an adjuvant microparticle composed of an amphiphilic polymer(s) whose hydrophobic segment(s) is/are poly (hydroxy acid); and a surfactant.

First, the amphiphilic polymer constituting the adjuvant microparticle is described. "Amphiphilic" means that the properties of both hydrophilicity and hydrophobicity are retained. When solubility of a certain portion in water is higher than those of other portions, the portion is said to be hydrophilic. The hydrophilic portion is preferably soluble in water, but even when the portion has poor solubility in water, it is sufficient if the solubility in water is higher than those of other portions. When solubility of a certain portion in water is lower than those of other portions, the segment is said to be hydrophobic. The hydrophobic portion is preferably insoluble in water, but even when the portion is soluble in water, it is sufficient if the solubility in water is lower than those of other portions.

The amphiphilic polymer means a polymer having the above-mentioned amphiphilicity as the whole molecule. The polymer means that the molecule has a molecular structure wherein a hydrophilic segment(s) or a hydrophobic segment(s) of the amphiphilic polymer, or the both, is/are constituted by a structure(s) in which minimum units (monomers) are repeated. The amphiphilic polymer is not restricted as long as it has a structure having a hydrophilic segment(s) and a hydrophobic segment(s), and may be a linear block polymer having a hydrophilic segment(s) and a hydrophobic segment(s) linked to each other; a branched polymer having a branch(es) in which a plurality of hydrophilic segments or hydrophobic segments, or both of these, exist; or a graft polymer in which a plurality of hydrophobic segments are grafted to a hydrophilic segment or a plurality of hydrophilic segments are grafted to a hydrophobic segment. The amphiphilic polymer is preferably a polymer having one hydrophilic segment, most preferably a linear block polymer having one each of a hydrophilic segment and a hydrophobic segment, or a graft polymer having a plurality of hydrophobic segments grafted on a hydrophilic segment backbone.

The amphiphilic polymers constituting the immunogenic composition may be a set of a plurality of types of amphiphilic polymers composed of constituent polymers having different hydrophilic portions and/or hydrophilic portions, or a set of amphiphilic polymers having the same constituent polymer but having a plurality of types of linking patterns, as long as the amphiphilic polymers have properties as an adjuvant microparticle. To achieve stable performance and enhanced productivity, the amphiphilic polymers are preferably a set of a small number of types of amphiphilic polymers, more preferably a set of mainly not more than 2 types of amphiphilic polymers, and still more preferably constituted by mainly a single type of amphiphilic polymer.

The hydrophobic segment of the amphiphilic polymer is poly(hydroxy acid). The poly(hydroxy acid) is not restricted, and preferably a biocompatible polymer which does not have a severely adverse effect upon administration to a living body. The biocompatibility herein means that LD50 in oral administration of the polymer to rats is not less than 2,000 mg/kg. Further, the polymer may be a copolymer of a plurality of types of hydroxy acids, and is preferably a polymer of not more than 2 types of hydroxy acids. Particularly preferred examples of the poly(hydroxy acid) include polyglycolic acid, polylactic acid, poly(2-hydroxybutyric acid), poly(2-hydroxyvaleric acid), poly(2-hydroxycaproic acid), poly(2-hydroxycapric acid) and poly(malic acid); and derivatives and copolymers of these macromolecular compounds; among which polylactic acid, polyglycolic acid, and poly(lactic-co-glycolic acid) copolymers are more preferred. Further, when the poly(hydroxy acid) is poly(lactic-co-glycolic acid), the composition ratio of the poly(lactic-co-glycolic acid) (lactic acid/glycolic acid) (mol/mol %) is not restricted as long as our purposes are achieved therewith, and the ratio is preferably 100/0 to 30/70, more preferably 60/40 to 40/60.

The hydrophilic segment of the amphiphilic polymer is not restricted, and preferably a biocompatible polymer, as in the hydrophobic segment. Further, to give a persistent adjuvant capacity to the adjuvant microparticle composed of an amphiphilic polymer(s), the segment is preferably a refractory polymer which is not easily decomposed in a living body or cell of a mammal or bird. Particular examples of the biocompatible and refractory polymer include polyethylene glycol, polyvinyl pyrrolidone, polyvinyl alcohol, polyethyleneimine, polyacrylic acid, polymethacrylic acid, poly-1,3-dioxolane, 2-methacryloyloxyethyl phosphoryl choline polymer, poly-1,3,6-trioxane, polyamino acid and refractory polysaccharides (e.g., cellulose, chitin, chitosan, gellan gum, alginic acid, hyaluronic acid, pullulan and dextran). When the hydrophilic segment is polyethylene glycol, polyvinyl pyrrolidone, polyvinyl alcohol, polyethyleneimine, polyacrylic acid, polymethacrylic acid, poly-1,3-dioxolane, 2-methacryloyloxyethyl phosphoryl choline polymer, poly-1,3,6-trioxane or polyamino acid, the amphiphilic polymer is preferably a linear block polymer having one each of a hydrophilic segment and a hydrophobic segment and, when the hydrophilic segment is a polysaccharide, the amphiphilic polymer is preferably a graft polymer having a plurality of hydrophobic segments grafted on a hydrophilic segment backbone. Further, the hydrophilic segment of the amphiphilic polymer is preferably polyethylene glycol or a refractory polysaccharide, and the polysaccharide is more preferably dextran.

The amphiphilic polymer having a hydrophobic segment(s) composed of poly(hydroxy acid) and a hydrophilic segment(s) preferably has water immiscibility as the whole polymer, in view of the antigen-encapsulation capacity of the immunogenic composition and persistency upon administration to a living body.

The average molecular weight of the hydrophilic segment of the amphiphilic polymer is not restricted and, in a block polymer wherein a hydrophilic segment(s) and a hydrophobic segment(s) are linearly linked to each other, the average molecular weight is preferably 1,000 to 50,000, more preferably 2,000 to 15,000. The term "block" herein means a portion in a polymer molecule, which portion is composed of not less than 5 monomer units and different from the other adjacent portion(s) in terms of the chemical structure or configuration. A polymer constituted by at least two blocks linearly linked to each other is called a "block polymer." Each block itself constituting the block polymer may be a random, alternating or gradient polymer composed of not less than 2 types of monomer units. Preferably, the block polymer is one wherein one unit of a polymer forming a hydrophilic segment and one unit of poly(hydroxy acid) are preferably linked together.

In a graft polymer having a hydrophobic segment(s) grafted on a hydrophilic segment backbone, the average molecular weight of the hydrophilic segment is preferably 1,000 to 100,000, more preferably 2,000 to 50,000, still more preferably 10,000 to 40,000. The number of the graft chains is preferably 2 to 50. The number of the graft chains can be calculated based on the ratio between the hydrophilic segment backbone and the hydrophobic segment backbone, and the average molecular weight of the hydrophobic segment, as obtained by $^1$H-NMR measurement, and the average molecular weight of the hydrophilic segment backbone used.

The preferred average molecular weight ratio between the hydrophobic segment and the hydrophilic segment varies depending on the amphiphilic polymer and, in a block polymer wherein a hydrophobic segment(s) and a hydrophilic segment(s) are linearly linked to each other, the average molecular weight ratio between the hydrophilic segment and the hydrophobic segment is preferably 1:1 or more, more preferably 1:2 or more, still more preferably 1:4 or more, especially preferably 1:4 or more and 1:25 or less.

Preferably, in a graft polymer having a plurality of hydrophobic segments grafted on a hydrophilic segment backbone, the average molecular weight ratio between the hydrophilic segment backbone portion and the whole hydrophobic segment graft chains is 1:3 or more, and the average molecular weight of each graft chain is 2,500 to 40,000. More preferably, the overall average molecular weight ratio is 1:5 or more and the average molecular weight of each graft chain is 5,000 to 40,000.

It should be noted that the above-mentioned average molecular weight is a number average molecular weight unless otherwise specified. The number average molecular weight is an average molecular weight calculated without weighting by the molecular size, and the number average molecular weights of the amphiphilic polymer and the polymers constituting the hydrophilic segment(s) of the amphiphilic polymer can be calculated as molecular weights in terms of polystyrene or pullulan as measured by gel permeation chromatography (GPC). Further, the average molecular weight of poly(hydroxy acid) can be calculated by measurement by nuclear magnetic resonance (NMR) based on the ratio between the peak integration value for terminal residues and the peak integration value for the others.

The amphiphilic polymer may be synthesized by a known method, and examples of the method include a method wherein a poly(hydroxy acid) polymer is added to a polymer to be used as a hydrophilic segment and condensation reaction is carried out with the resulting mixture to produce an amphiphilic polymer; a method wherein activated hydroxy acid monomers are added to a polymer to be used as a hydrophilic segment and polymerization reaction is carried out with the resulting mixture to produce an amphiphilic polymer; and a method wherein, conversely, monomers to constitute a hydrophilic segment are added to a hydrophobic segment which is a poly(hydroxy acid) polymer and polymerization reaction is carried out with the resulting mixture.

For example, an amphiphilic polymer constituted by polyethylene glycol and poly(hydroxy acid) can be produced by a method in which activated hydroxy acid monomers are added to polyethylene glycol in the presence of a tin catalyst to perform polymerization reaction for introduction of poly (hydroxy acid), thereby producing an amphiphilic block polymer [Journal of Controlled Release, 71, p. 203-211 (2001)].

Further, for example, a graft-type amphiphilic polymer constituted by a polysaccharide and a poly(hydroxy acid) graft chain(s) can be produced as described in (1), (2) or (3) below:

(1) a method wherein, in the presence of a tin catalyst, activated hydroxy acid monomers are added to a polysaccharide to perform polymerization reaction for introduction of poly(hydroxy acid), thereby producing a graft-type amphiphilic polymer [Macromolecules, 31, p. 1032-1039 (1998)];

(2) a method wherein unprotected hydroxyl groups in part of a polysaccharide in which most of its hydroxyl groups are protected by substituents are activated with a base, and activated hydroxy acid monomers are added thereto to introduce a graft chain(s) composed of poly (hydroxy acid), followed by finally removing the protecting groups, thereby producing a graft-type amphiphilic polymer [Polymer, 44, p. 3927-3933, (2003)]; and (3) a method wherein condensation reaction of a copolymer of poly(hydroxy acid) with a polysaccharide is carried out using a dehydrating agent and/or a functional-group-activating agent, to produce a graft-type amphiphilic polymer [Macromolecules, 33, p. 3680-3685 (2000)].

The adjuvant microparticle is described below. The adjuvant microparticle is a microparticle having an adjuvant capacity, and the adjuvant capacity means a capacity with which the immune response upon administration of an antigen to a living body can be caused at a higher level than in administration of the antigen alone. Further, the adjuvant microparticle is a microparticle composed of an amphiphilic polymer(s), and an antigen(s) is/are encapsulated in the adjuvant microparticle to form an antigen-adjuvant microparticle complex, which complex constitutes the microparticle as an effective ingredient of the immunogenic composition.

The structure of the adjuvant microparticle is not restricted, and a structure wherein a hydrophilic segment(s) of the amphiphilic polymer(s) is/are contained inside the adjuvant microparticle and a hydrophobic segment(s) of the amphiphilic polymer(s) is/are contained as an outer layer is preferred in view of stably retaining the encapsulated antigen(s).

The type of the antigen encapsulated in the adjuvant microparticle is not restricted, and may be a peptide, protein, glycoprotein, glycolipid, lipid, carbohydrate, nucleic acid or polysaccharide; or a virus, bacterial cell, allergenic substance, tissue or cell comprising these. Specific examples of the antigen include pollen-derived antigens, hepatitis A virus-derived antigens, hepatitis B virus-derived antigens, hepatitis C virus-derived antigens, hepatitis D virus-derived antigens, hepatitis E virus-derived antigens, hepatitis F virus-derived antigens, HIV virus-derived antigens, influenza virus-derived antigens, herpes virus (HSV-1, HSV-2)-derived antigens, anthrax-derived antigens, chlamydia-derived antigens, pneumococcus-derived antigens, Japanese encephalitis virus-derived antigens, measles virus-derived antigens, rubella virus-derived antigens, *Clostridium tetani*-derived antigens, chickenpox virus-derived antigens, SARS virus-derived antigens, EB virus-derived antigens, papilloma virus-derived antigens, *Helicobacter pylori*-derived antigens, rabies virus-derived antigens, West Nile virus-derived antigens, hantavirus-derived antigens, *Streptococcus*-derived antigens, *Staphylococcus*-derived antigens, *Bordetella pertussis*-derived antigens, *Mycobacterium tuberculosis*-derived antigens, *Plasmodium*-derived antigens, poliovirus-derived antigens, antigens derived from various zoonotic infections, cancer antigens, and antigens derived from various food allergies.

The encapsulated antigen does not need to be a single antigen. Immune responses may be induced against cancer cells, bacteria, viruses or the like which are constituted by a plurality of constituents. In such cases, the antigen may be a plurality of types of proteins or the like which may cause immune responses, or a mixture of substances whose types cannot be specified. Further, inclusion of a plurality of types of antigens positively inducing immune responses against the plurality of types of antigens is one of the modes of use of the immunogenic composition. Preferably, not more than 3 types, more preferably a single type of antigen(s) is/are encapsulated in the adjuvant microparticle.

The antigen-adjuvant microparticle complex may change the retention capacity of the contained antigen depending on the type(s) and the preparation method(s) of the polymer(s) constituting the adjuvant microparticle. Possible examples of the mechanism by which immunogenicity is provided by the antigen-adjuvant microparticle complex include a plurality of processes such as a process wherein the antigen released from the adjuvant microparticle is recognized by immunocompetent cells, and a process wherein the adjuvant microparticle itself is recognized by immunocompetent cells. An excellent effect can be obtained also by the synergistic effect of these processes.

The type of the immune response induced by the process in which the antigen-adjuvant microparticle complex makes immunocompetent cells recognize the antigen varies depending on the type of the process, and a preferred process may be selected depending on the type of the immune response to be induced and the site of administration. That is, in a preferred mode of use, the antigen does not necessarily need to be released from the antigen-adjuvant microparticle complex, and the mode with which the optimum immunogenicity of interest is realized is attained by optimization depending on the antigen and the type of immune response to be activated. However, when the antigen is extremely quickly released from the antigen-adjuvant microparticle complex, a long-term continuous immune-activating action, which is an excellent property, cannot be obtained so that, preferably, not less than 10% of the antigen in the antigen-adjuvant microparticle complex is still retained in the living body as the complex one week after the administration and, more preferably, not less than 50% of the antigen is still encapsulated one week after the administration. These release behaviors can be confirmed by in vitro evaluation mimicking the in vivo environment.

The antigen-adjuvant microparticle complex attains a good effect even in a particle state wherein the complex is associated together. "Association" herein means that two or more particles are bound together by an interparticle force or via another substance, to form an aggregate. The interparticle force is not restricted, and examples thereof include the hydrophobic interaction, hydrogen bond and van der Waals force. The association is not restricted to the state where the microparticles are in contact with each other, and a substance having affinity to the microparticles may exist between the microparticles, or the microparticles may be dispersed in a matrix. As the substance having affinity to the microparticles, or the matrix, a polymer is preferred, and an amphiphilic polymer whose hydrophobic portion is poly(hydroxy acid) and which has the same constituent as that of the adjuvant microparticle is more preferred. Particular examples thereof include amphiphilic polymers each composed of a polysaccharide backbone and a poly(hydroxy acid) graft chain(s), block polymers each composed of polyethylene glycol and poly(hydroxy acid), and poly(hydroxy acid).

The association of the antigen-adjuvant microparticle complex may be either in a state where reisolation occurs upon the use or in a state where reisolation does not occur upon the use. It should be noted that, even when the shape of the particle composed of the antigen-adjuvant microparticle complex associated together is in a state from which the association of the complex cannot be known, the particle is regarded as having been formed by association of the complex as long as the production process of the particle comprises the step of associating the complex.

The average particle size of the antigen-adjuvant microparticle complex or the particle formed by association of the complex is preferably 0.1 to 50 μm, more preferably 0.1 to 10 μm. In particular, the average particle size of the antigen-adjuvant microparticle complex is preferably 0.1 to 1 μm, more preferably 0.1 to 0.5 μm, and the average particle size of the antigen-adjuvant microparticle complex is preferably 0.1 to 50 μm, more preferably 0.1 to 10 μm, still more preferably 1 to 10 μm. The average particle size of the antigen-adjuvant microparticle complex or the particle formed by association of the complex can be measured directly by image analysis using a scanning electron microscope (SEM, e.g., S-4800 manufactured by Hitachi, Ltd.).

The antigen-adjuvant microparticle complex or the particle formed by association of the complex has an effect to enhance the immunogenicity of the encapsulated antigen. We discovered that the immunogenicity of the encapsulated antigen can be further enhanced by encapsulating as an effective ingredient a surfactant(s) in the immunogenic microparticle composed of the antigen-adjuvant microparticle complex or the particle formed by association of the complex (hereinafter referred to as "immunogenic microparticle"). That is, the immunogenic microparticle as an effective ingredient of the immunogenic composition comprises as a constituent a surfactant encapsulated therein.

The surfactant is not restricted and specific examples of the surfactant include polysorbate 20, polysorbate 40, polysorbate 60, polysorbate 65, polysorbate 80, polysorbate 85, glycerin monooleate, sorbitan monooleate, polyethylene glycol monooleate, ethylene glycol monostearate, glycerin monostearate, sorbitan monostearate, propylene glycol monostearate, polyethylene glycol monostearate, sorbitan monopalmitate, glycerin monomyristate, sorbitan monolaurate, polyethylene glycol monolaurate, sorbitan trioleate, sorbitan tristearate, polyoxyethylene hydrogenated castor oil, polyoxyethylene propylene glycol copolymers, polyethylene glycol, polyvinyl alcohol, polyoxyethylene alkyl ether, fatty acid diethanol amide (e.g., stearic acid diethanol amide, oleic acid diethanol amide and lauric acid diethanol amide), lecithin, sodium fatty acid (e.g., sodium stearate, sodium oleate and sodium laurate), sodium alkyl sulfate, polyoxyethylene octyl phenyl ether and alkyl glycoside. The surfactant may be either a single type or 2 or more types.

The surfactant is preferably one proven as a pharmaceutical additive. Specific examples of surfactants proven as pharmaceutical additives include polysorbate 20, polysorbate 40, polysorbate 60, polysorbate 65, polysorbate 80, polysorbate 85, glycerin monooleate, sorbitan monooleate, polyethylene glycol monooleate, ethylene glycol monostearate, glycerin monostearate, sorbitan monostearate, propylene glycol monostearate, polyethylene glycol monostearate, sorbitan monopalmitate, glycerin monomyristate, sorbitan monolaurate, polyethylene glycol monolaurate, sorbitan trioleate, sorbitan tristearate, polyoxyethylene hydrogenated castor oil, polyoxyethylene propylene glycol copolymers, polyethylene glycol, polyvinyl alcohol, polyoxyethylene alkyl ether, fatty acid diethanol amide (e.g., stearic acid diethanol amide, oleic acid diethanol amide and lauric acid diethanol amide), lecithin, sodium fatty acid (e.g., sodium stearate, sodium oleate and sodium laurate) and sodium alkyl sulfate.

The surfactant is preferably a nonionic surfactant. Specific examples of nonionic surfactant include polysorbate 20, polysorbate 40, polysorbate 60, polysorbate 65, polysorbate 80, polysorbate 85, glycerin monooleate, sorbitan monooleate, polyethylene glycol monooleate, ethylene glycol monostearate, glycerin monostearate, sorbitan monostearate, propylene glycol monostearate, polyethylene glycol monostearate, sorbitan monopalmitate, glycerin monomyristate, sorbitan monolaurate, polyethylene glycol monolaurate, sorbitan trioleate, sorbitan tristearate, polyoxyethylene hydrogenated castor oil, polyoxyethylene propylene glycol copolymers, polyethylene glycol, polyvinyl alcohol, polyoxyethylene alkyl ether and fatty acid diethanol amide (e.g., stearic acid diethanol amide, oleic acid diethanol amide and lauric acid diethanol amide).

Among the surfactants, surfactants comprising a fatty acid ester structure are preferably used. Specific examples of the fatty acid ester structure include lauric acid ester, palmitic acid ester, stearic acid ester, oleic acid ester and hydrogenated castor oil, and preferred specific examples of the fatty acid ester structure include lauric acid ester, oleic acid ester and hydrogenated castor oil. Specific examples of the surfactants comprising a fatty acid ester structure include polysorbate 20, polysorbate 40, polysorbate 60, polysorbate 65, polysorbate 80, polysorbate 85, glycerin monooleate, sorbitan monooleate, polyethylene glycol monooleate, ethylene glycol monostearate, glycerin monostearate, sorbitan monostearate, propylene glycol monostearate, polyethylene glycol monostearate, sorbitan monopalmitate, glycerin monomyristate, sorbitan monolaurate, polyethylene glycol monolaurate, sorbitan trioleate, sorbitan tristearate and polyoxyethylene hydrogenated castor oil.

Further, in terms of structures other than fatty acid esters, the surfactant preferably comprises a biocompatible molecule. Specific examples of the biocompatible molecule other than fatty acid esters in the surfactant include amino acids, nucleic acids, phosphoric acid, sugars (e.g., monosaccharides such as sucrose, sorbitol, mannose and glucose), polyethylene glycol and glycerin. The biocompatible molecule is preferably constituted by a monosaccharide(s) and/or polyethylene glycol, and is more preferably sorbitol. Specific examples of the surfactant comprising a biocompatible molecule as a structure other than fatty acid esters include polysorbate 20, polysorbate 40, polysorbate 60, polysorbate 65, polysorbate 80, polysorbate 85, glycerin monooleate, sorbitan monooleate, polyethylene glycol monooleate, ethylene glycol monostearate, glycerin monostearate, sorbitan monostearate, propylene glycol monostearate, polyethylene glycol monostearate, sorbitan monopalmitate, glycerin monomyristate, sorbitan monolaurate, polyethylene glycol monolaurate, sorbitan trioleate, sorbitan tristearate and polyoxyethylene hydrogenated castor oil, and preferred specific examples of the surfactant include polysorbate 80, polysorbate 20, sorbitan trioleate and polyoxyethylene hydrogenated castor oil.

In the immunogenic microparticle, the surfactant is encapsulated in a microparticle. The encapsulation of a surfactant herein means a state where a surfactant is present in the inner portion of the microparticle, and the surfactant may be present in the entire inner portion of the microparticle or may be localized in a part of the inner portion of the microparticle. In terms of the encapsulation of a surfactant, the surfactant is regarded as being encapsulated in the particle when the production process of the microparticle comprises the step of encapsulating a surfactant in the microparticle. The amount of the surfactant(s) in the immunogenic microparticle is not restricted and is preferably 0.01 to 50% (w/w), more preferably 0.1 to 20% (w/w), still more preferably 1 to 10% (w/w) with respect to the amount of the amphiphilic polymer fed in the production process of the immunogenic microparticle. The amount of the surfactant(s) in the immunogenic microparticle is measured by extracting the surfactant(s) from the immunogenic microparticle using a solvent in which the amphiphilic polymer can be dissolved, and purifying the resulting extract, followed by analyzing the purified extract by liquid chromatography using a reverse-phase column, thereby measuring the amount of the surfactant(s) contained in the extract. Based on the amount of the surfactant(s) contained in the extract, the amount of the surfactant(s) with respect to the amount of the amphiphilic polymer(s) fed in the production process of the immunogenic microparticle is calculated.

The method of producing the immunogenic microparticle is not restricted and, when the immunogenic microparticle is constituted by an antigen-adjuvant microparticle complex, examples of the method by which the immunogenic microparticle can be produced include a method comprising: (a) mixing an aqueous solvent A wherein an antigen(s) is/are dissolved and a water-immiscible organic solvent B wherein an amphiphilic polymer(s) is/are dissolved, to form a reversed-phase emulsion; and (b) removing the solvent from the reversed-phase emulsion to obtain an immunogenic microparticle. Steps (a) and (b) are described below.

As the aqueous solvent A in step (a), water, or an aqueous solution containing a water-soluble component is used. Examples of the water-soluble component include inorganic salts, sugars, organic salts and amino acids.

The water-immiscible organic solvent B in step (a) is preferably a solvent in which the poly(hydroxy acid) of the amphiphilic polymer is soluble and the polymer constituting the hydrophilic segment is poorly soluble or insoluble, and, preferably, the solvent can be removed by sublimation by freeze drying. The solubility of the water-immiscible organic solvent B in water is preferably not more than 30 g (water-immiscible organic solvent B)/100 ml (water). Particular examples of the water-immiscible organic solvent B include ethyl acetate, isopropyl acetate, butyl acetate, dimethyl carbonate, diethyl carbonate, methylene chloride and chloroform.

The ratio between the water-immiscible organic solvent B and the aqueous solvent A is 1,000:1 to 1:1, preferably 100:1 to 1:1. The concentration of the amphiphilic polymer(s) in the water-immiscible organic solvent B varies depending on the types of the water-immiscible organic solvent B and the amphiphilic polymer(s), and the concentration is 0.01 to 90% (w/w), preferably 0.1 to 50% (w/w), more preferably 1 to 20% (w/w).

By dissolving a surfactant(s) in either the aqueous solvent A or the water-immiscible organic solvent B used in the step (a), the surfactant(s) can be encapsulated in the immunogenic microparticle. The amount of the surfactant(s) added in step (a) is preferably 0.01 to 50% (w/w), more preferably 0.1 to 20% (w/w), still more preferably 1 to 10% (w/w) with respect to the amount of the amphiphilic polymer(s) dissolved in the water-immiscible organic solvent B.

In step (a), in the process of formation of a reversed-phase emulsion with an aqueous solvent A and a water-immiscible organic solvent B in which an amphiphilic polymer(s) is/are dissolved, the reversed-phase emulsion may be formed using, depending on the pharmaceutical purpose, a water-immiscible organic solvent B in which two or more types of amphiphilic polymers are dissolved.

In step (a), to aid the formation of a reversed-phase emulsion and to form a uniform and fine reversed-phase emulsion, an additive(s) may be added. The additive is preferably a compound selected from $C_3$-$C_6$ alkyl alcohols, $C_3$-$C_6$ alkyl amines and $C_3$-$C_6$ alkyl carboxylic acids. The structure of each alkyl chain in these additives is not restricted, and the alkyl chain may have either a linear structure or a branched structure, and may be either a saturated alkyl or an unsaturated alkyl. The additive is especially preferably tert-butanol, iso-propanol or pentanol.

In step (b), the method of removal of the solvent from the reversed-phase emulsion is not restricted, and examples thereof include heating, drying under reduced pressure, dialysis, freeze drying, centrifugation, filtration and reprecipitation, and combinations thereof. Among the methods of removal of the solvent from the reversed-phase emulsion, freeze drying is preferred since it causes less structural changes due to fusion of particles in the reversed-phase emulsion, or the like. The conditions and the apparatus for the freeze drying are those which allow inclusion of a freezing process and a drying step under reduced pressure, and the process of freeze drying especially preferably comprises prior freezing, primary drying under reduced pressure at low temperature, and secondary drying under reduced pressure, which are conventionally carried out in freeze drying. For example, when a dispersion of an antigen-adjuvant microparticle complex in a water-immiscible solvent is to be obtained, the reversed-phase emulsion is cooled/frozen to not more than the melting points of the aqueous solvent A and the water-immiscible organic solvent B constituting the reversed-phase emulsion, and then dried under reduced pressure, to obtain freeze-dried adjuvant microparticles. The temperature for the prior freezing may be experimentally determined as appropriate depending on the solvent composition, and is preferably not more than −20° C. The degree of reduction of the pressure during the drying process may also be determined as appropriate depending on the solvent composition, and is preferably not more than 3,000 Pa, more preferably not more than 500 Pa, in view of shortening of the drying time. The freeze drying is preferably carried out using a freeze dryer for laboratory use which has a cold trap and can be connected to a vacuum pump, or a shelf-type vacuum freeze dryer used for production of pharmaceuticals or the like. After the prior freezing with liquid nitrogen, a cooling medium or the like, the drying under reduced pressure may be carried out with cooling or at room temperature using a vacuum device such as a vacuum pump.

When the immunogenic microparticle is constituted of a microparticle composed of an antigen-adjuvant microparticle complex associated together, production examples of the immunogenic microparticle include a method comprising: (a') mixing an aqueous solvent A wherein an antigen(s) is/are dissolved and a water-immiscible organic solvent B wherein an amphiphilic polymer(s) is/are dissolved, to form a reversed-phase emulsion; (b') removing the solvent from the reversed-phase emulsion to obtain an antigen-adjuvant microparticle complex; and (c') introducing an antigen-adjuvant microparticle complex dispersion C to a liquid phase D comprising a surface modifier, followed by removing the dispersion medium; by which the immunogenic microparticle composed of an antigen-adjuvant microparticle complex associated together can be obtained.

The conditions of the aqueous solvent A in step (a') and the water-immiscible organic solvent B in step (b') are the same as in the above-mentioned steps (a) and (b).

The method employed to remove the solvent from the reversed-phase emulsion in step (b') is the same as the above-mentioned method in step (b).

In step (c'), the dispersion medium to be used to disperse the antigen-adjuvant microparticle complex to prepare the complex dispersion C is not restricted, and when the adjuvant microparticle has, in its inner portion, a hydrophilic portion composed of a hydrophilic segment(s) of the hydrophilic polymer, and has, in the outer layer, a hydrophobic portion composed of a hydrophobic segment(s) of the hydrophilic polymer, the dispersion medium is preferably a solvent in which poly(hydroxy acid) of the amphiphilic polymer is soluble and the polymer constituting the hydrophilic segment is substantially insoluble, for the purpose of protecting the structure of the adjuvant microparticle. In this case, the solvent may be either a water-immiscible organic solvent or a water-miscible organic solvent. Particular examples of the solvent in which the poly(hydroxy acid) of the amphiphilic polymer is soluble and the polymer constituting the hydrophilic segment is substantially insoluble include ethyl acetate, isopropyl acetate, butyl acetate, dimethyl carbonate, diethyl carbonate, methylene chloride, chloroform, dioxane, toluene and xylene.

Preferably, the liquid phase D in step (c') is one in which a surface modifier is soluble, and has a higher boiling point than the dispersion medium of the dispersion C. The liquid phase D may be any of an aqueous solvent, water-immiscible organic solvent and water-miscible organic solvent. As the aqueous solvent, water or an aqueous solution containing a water-soluble component is preferred, and examples of the water-soluble component include inorganic salts, sugars, organic salts and amino acids. Examples of the water-immiscible organic solvent include silicone oil, sesame oil, soybean oil, corn oil, cottonseed oil, coconut oil, linseed oil, mineral oil, castor oil, hydrogenated castor oil, liquid paraffin, n-hexane, n-heptane, glycerol and oleic acid. Examples of the water-miscible organic solvent include glycerin, acetone, ethanol, acetic acid, dipropylene glycol, triethanolamine and triethylene glycol. Among these, the liquid phase D is preferably an aqueous solvent or a water-miscible organic solvent. When the liquid phase D is an aqueous solvent and the dispersion medium is a water-immiscible organic solvent, the obtained suspension of an antigen-adjuvant microparticle complex is in the form of the so-called "solid-in-oil-in-water" (S/O/W) emulsion and, when the liquid phase D is a water-immiscible organic solvent or a water-miscible organic solvent and immiscible in the dispersion medium, the suspension is in the form of a solid-in-oil-in-oil (S/O1/O2) emulsion.

By dissolving a surfactant(s) in the aqueous solvent A or water-immiscible organic solvent B used in step (a') or in the dispersion C used in step (c'), the surfactant(s) can be encapsulated in the immunogenic microparticle composed of an antigen-adjuvant microparticle complex associated together. On the other hand, when a surfactant(s) is/are dissolved in the liquid phase D used in step (c'), the surfactant(s) is/are bound to the surface of the immunogenic microparticle composed of an antigen-adjuvant microparticle complex associated together so that the desired effect cannot be obtained. The amount of the surfactant(s) added in step (a') or (c') is preferably 0.01 to 50% (w/w), more preferably 0.1 to 20% (w/w), still more preferably 1 to 10% (w/w) with respect to the amount of the amphiphilic polymer(s) dissolved in the water-immiscible organic solvent.

The surface modifier to be added in step (c') is preferably a compound which stabilizes the water-oil interface of the S/O/W emulsion or the oil-oil interface of the S/O1/O2 emulsion, which compound has a property to enhance the colloidal stability of the particle composed of the antigen-adjuvant microparticle complex associated together. Enhancement of the colloidal stability herein means prevention or delaying of aggregation, in the solvent, of the particles composed of the antigen-adjuvant microparticle complex associated together. The surface modifier may be a single agent or a mixture of a plurality of agents.

The surface modifier is preferably a hydrophilic polymer or an amphiphilic compound.

The hydrophilic polymer as a surface modifier is preferably polyethylene glycol, polyvinyl pyrrolidone, polyvinyl alcohol, polyethyleneimine, polyacrylic acid, polymethacrylic acid, poly-1,3-dioxolane, 2-methacryloyloxyethyl phosphoryl choline polymer, poly-1,3,6-trioxane, polyamino acid, peptide, protein or sugar polysaccharide, or an analogue of any of these. Examples of the analogue of the hydrophilic polymer include, but are not limited to, those prepared from hydrophilic polymers by, for example, partial modification of hydrophobic groups such as long-chain alkyl.

The polyethylene glycol analogue as a surface modifier is preferably "Pluronic" (registered trademark of BASF) commercially available from BASF, or its equivalent.

The polyamino acid as a surface modifier is preferably polyaspartic acid or polyglutamic acid, or its analogue. Analogues prepared by introducing long-chain alkyl to a part of polyaspartic acid or polyglutamic acid are more preferred.

Examples of the peptide as a surface modifier include basic peptides, and the protein as a surface modifier is preferably gelatin, casein or albumin in view of enhancement of dispersibility of the particles. Preferred examples of the protein also include antibodies.

The sugar as a surface modifier is preferably a monosaccharide, oligosaccharide or polysaccharide. The polysaccharide is preferably cellulose, chitin, chitosan, gellan gum, alginic acid, hyaluronic acid, pullulan or dextran, and cholesterol-bearing pullulan is especially preferred in view of enhancement of dispersibility of the particles. An analogue of any of cellulose, chitin, chitosan, gellan gum, alginic acid, hyaluronic acid, pullulan and dextran is preferred.

The peptide, protein or sugar as a surface modifier is especially preferably an analogue prepared by, for example, partial modification of hydrophobic groups such as long-chain alkyl, or an analogue prepared by modifying the above-mentioned hydrophilic polymer or amphiphilic compound.

Preferred examples of the amphiphilic compound as a surface modifier include nonionic activators such as polyoxyethylene polypropylene glycol copolymers, sucrose fatty acid esters, polyethylene glycol fatty acid esters, polyoxyethylene sorbitan monofatty acid esters, polyoxyethylene sorbitan difatty acid esters, polyoxyethylene glycerol monofatty acid esters, polyoxyethylene glycerol difatty acid esters, polyglycerol fatty acid esters, polyoxyethylene castor oil and polyoxyethylene hydrogenated castor oil; alkyl sulfates such as sodium lauryl sulfate, ammonium lauryl sulfate and sodium stearyl sulfate; and lecithin.

The volume ratio between the dispersion medium in which the antigen-adjuvant microparticle complex is dispersed and the liquid phase D is 1,000:1 to 1:1,000, preferably 100:1 to 1:100. The association number of the antigen-adjuvant microparticle complex obtained varies depending on this volume ratio, and, as the ratio of the lipid phase D increases, a dispersion, in water, of particles composed of a larger number of the antigen-adjuvant microparticle complex associated together is obtained, while, as the ratio of the lipid phase D decreases, the association number decreases. When the ratio of the liquid phase D is smaller than a solution ratio of 1:4, most of the particles in the dispersion in water are each constituted of a single antigen-adjuvant microparticle complex. Thus, by controlling the volume ratio of the liquid phase D in the series of processes for production of the particle composed of the antigen-adjuvant microparticle complex associated together, the antigen-adjuvant microparticle complex and the particle composed of the complex associated together can be selectively prepared.

When the dispersion medium containing the antigen-adjuvant microparticle complex is mixed with the liquid phase D, a stirring device such as a magnetic stirrer, turbine stirrer, homogenizer, membrane emulsification apparatus equipped with a porous membrane, or the like may be used as required.

The liquid phase D may contain, in addition to the surface modifier, various additives such as a buffer, antioxidant, salt, polymer and/or sugar depending on the pharmaceutical purpose. Further, the dispersion medium in which the antigen-adjuvant microparticle complex is to be dispersed may contain various additives soluble in the dispersion medium such as an acidic compound, basic compound, amphiphilic polymer and/or biodegradable polymer, for the purpose of controlling the release rate of the encapsulated antigen(s) by degradation or disintegration of the complex.

Further, an emulsifying operation of the formed solid-in-oil-in-water (S/O/W) emulsion or solid-in-oil-in-oil (S/O1/O2) emulsion may be carried out for the purpose of producing a finer particle composed of the antigen-adjuvant microparticle complex associated together. The method of emulsification is not restricted as long as a stable emulsion can be prepared thereby, and examples thereof include methods by stirring and methods using a high-pressure homogenizer, high-speed homomixer or the like.

When the antigen-adjuvant microparticle complex is once dispersed in a dispersion medium and the obtained dispersion C is added to the liquid phase D containing a surface modifier, a suspension of the particle composed of a desired adjuvant microparticle associated together can be obtained by removal of the dispersion medium. The method of removal of the dispersion medium is not restricted, and examples thereof include solvent evaporation, dialysis, freeze drying, centrifugation, filtration and reprecipitation, among which solvent evaporation and freeze drying are especially preferred. When an aqueous solvent is used as the liquid phase D, an aqueous dispersion of the particle composed of the antigen-adjuvant microparticle complex associated together can be obtained by this step.

Preferably, the surface modifier is bound to the immunogenic microparticle. The binding herein may be either a non-covalent bond or covalent bond. The non-covalent bond is preferably a hydrophobic interaction, and may also be an electrostatic interaction, hydrogen bond or van der Waals force, or a combination of these bonds. In a non-covalent bond, poly(hydroxy acid) of the immunogenic microparticle containing the amphiphilic polymer is preferably bound to the hydrophobic portion of the surface modifier by a hydrophobic interaction and, in this case, the dispersion medium for the antigen-adjuvant microparticle complex in the microparticle dispersion is preferably water, buffer, physiological saline, aqueous surface modifier solution or hydrophilic solvent.

The immunogenic composition is a composition which can induce an immune response in a living body and contains the immunogenic microparticle as an effective ingredient. The type of the immune response induced by the immunogenic composition is not restricted. Examples of the type of the immune response induced include the Th1 immune response and the Th2 immune response, and it is known that one of these immune responses is predominantly induced depending on the antigen, the site of administration, and the type of the administration method. Our compositions may induce both of the Th1 and Th2 immune responses. The Th1 immune response can be effectively induced by the antigen-adjuvant microparticle complex having a small particle size, or by the particle composed of the complex associated together, as shown in Examples. The degrees of the Th1 immune response and the Th2 immune response can be evaluated by various known methods. For example, in a mouse, the amount of production of the IgG2a antibody is known to be an index of the Th1 immune response. Further, as indices of the Th2 immune response, the amounts of the IgG1 antibody and the total IgG antibody are known.

The immunogenic composition can realize a high immune-activating capacity by additional inclusion of an immune-activating substance. The immune-activating substance may be either contained in the outside of the adjuvant microparticle or encapsulated therein, and the substance is preferably encapsulated in the adjuvant microparticle. The immune-activating substance is not restricted as long as it can function as an immune-activating substance, and examples thereof include oils, aluminum salts, calcium salts, gel-forming polymers, immune-activating cytokines and TLR receptor ligands, among which immune-activating cytokines and TLR receptor ligands are preferred.

Examples of the immune-activating cytokines include interleukin 12, interferon α, interleukin 18, TNFα, interleukin 6, NO, interferon γ and interferon β.

Examples of the TLR receptor ligands include lipoproteins; double-stranded RNAs such as poly I:C and poly I:CLC; flagellin; single-stranded RNAs; CpG; profilin; MPL; QS21; and TDM, among which nucleic acids such as double-stranded RNAs, single-stranded RNAs and CpG are preferred, and CpG is more preferred. The CpG herein means unmethylated CpG (cytosine-guanine)-motif DNAs existing in viruses, bacteria and the like (see Japanese Translated PCT Patent Application Laid-open No. 2001-503254). Various effective sequences are reported as CpG motifs, and the type of the sequence is not restricted as long as it has an immune-activating capacity, and the sequence may be prepared using base analogues or may be selected from various types of modified products.

When the immunogenic composition is used as a pharmaceutical composition or a vaccine, various pharmaceutically useful additives may be contained in addition to the amphiphilic polymer, hydrophilic active substance, surface modifier and dispersion medium. Examples of the additives which may be added include buffers, antioxidants, salts, polymer and sugars.

The method of induction of an immune response using the immunogenic composition is not restricted, and the immunogenic composition may be either administered to a living body or brought into contact with immunocompetent cells removed to the outside of a living body. The method of administration of the immunogenic composition to a living body is not restricted, and examples thereof include subcutaneous administration, intradermal administration, intramuscular administration, transnasal administration, pulmonary administration, oral administration, transdermal administration, sublingual administration, intravaginal administration, intraperitoneal administration and lymph node administration, among which intradermal administration and subcutaneous administration are preferred.

In terms of the amount of the immunogenic composition to be used upon induction of the immune response, the necessary amount of the antigen required for induction of the immune reaction of interest is set appropriately depending on the type of the antigen, administration method, and number of doses. For example, when the immunogenic composition is subcutaneously administered to human to induce an immune response, the composition is administered at a dose of 0.01 to 1,000 µg each time in terms of the amount of antigen contained in the immunogenic composition. The number of doses may also be appropriately set similarly to the dose, and the immune response can be induced by 1 to 10 times of administration since the immunogenic composition has an action to induce an immune response continuously.

The living body to which the immunogenic composition is administered may be either human or a non-human animal, and the living body is preferably human; or pig, cow, bird, sheep, horse, donkey, goat, camel, dog, cat, ferret, rabbit, monkey, rat, mouse or guinea pig, which is kept as a livestock, pet animal or experimental animal.

EXAMPLES

Examples are described below, but this disclosure is not restricted by these Examples.

Example 1 Synthesis of Dextran-Poly(Lactic-Co-Glycolic Acid) (PLGA)

(1-1) Synthesis of TMS-Dextran (Compound (1))

Dextran (Nacalai Tesque; special grade according to Nacalai standards; number average molecular weight, 13,000; 5.0 g) was added to formamide (100 ml), and the resulting mixture was heated to 80° C. To this solution, 1,1,1,3,3,3-hexamethyldisilazane (100 ml) was added dropwise for 20 minutes. Thereafter, the resulting mixture was stirred at 80° C. for 2 hours. After completion of the reaction, the reaction solution was allowed to cool to room temperature, and two layers were separated from each other with a separatory funnel. The upper layer was concentrated under reduced pressure, and methanol (300 ml) was added thereto, followed by filtering and drying the obtained solids, to obtain TMS-dextran (Compound (1)) (11.4 g) as white solids.

(1-2) Synthesis of Dextran-PLGA (Compound (2))

Compound (1) (0.5 g) and potassium tert-butoxide (35 mg) were dried under heat under reduced pressure for 2 hours, and tetrahydrofuran (10 ml) was added thereto, followed by stirring the resulting mixture for 1.5 hours at room temperature. To this solution, a solution of (DL)-lactide (0.56 g) and glycolide (0.9 g) in tetrahydrofuran (15 ml) was added dropwise, and the resulting mixture was stirred for 5 minutes, followed by adding 2 drops of acetic acid to stop the reaction. After completion of the reaction, the solvent was concentrated under reduced pressure, and reprecipitation purification with the chloroform-methanol system and the chloroform-diethyl ether system was carried out, to obtain white solids, which were then dissolved in chloroform (9 ml). To the resulting solution, trifluoroacetic acid (1.0 ml) was added, and the resulting mixture was stirred at room temperature for 30 minutes. After completion of the reaction, the solvent was evaporated under reduced pressure, and the residue was dissolved in chloroform (10 ml), followed by adding the resulting solution dropwise to diethyl ether which had been preliminarily cooled to 0° C. and filtering the obtained product, to obtain an amphiphilic polymer dextran-PLGA as white solids (Compound (2)). It was determined by $^1$H-NMR measurement that the number average molecular weight of the PLGA graft strands of the dextran-PLGA is 5571 and the graft chain number is 30.

Example 2 Preparation of Immunogenic Microparticles (Particles (1) to (10) and Comparative Particles (1) and (2))

In 100 µl of dimethyl carbonate, 5 mg of the dextran-poly(lactic-co-glycolic acid) (PLGA) in Example 1 (Compound (2)) was dissolved, to prepare 50 mg/ml amphiphilic polymer solution (B). To the amphiphilic polymer solution (B), 20 µl of tert-butanol was added, and 50 µl of 0.025% (w/v) aqueous CEA (carcinoembryonic antigen) (COSMO BIO Co., Ltd.) solution (A) was added dropwise thereto, followed by stirring the resulting mixture with a vortex mixer to produce a reversed-phase emulsion.

The reversed-phase emulsion was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours. The obtained solids were dispersed in 200 µl of dimethyl carbonate, to prepare a dispersion (C). The dispersion (C) was added dropwise to 2 ml of an aqueous solution containing 10% (w/v) surface modifier (polyvinyl alcohol or Pluronic F-68) shown in Table 1, and the resulting mixture was stirred and emulsified with a vortex mixer, to prepare an S/O/W emulsion. From the S/O/W emulsion, dimethyl carbonate was removed by solvent evaporation, to prepare an immunogenic microparticle suspension. The suspension was transferred to a 15-ml tube, and subjected to centrifugation at 8,000 rpm for 10 minutes, to precipitate the particles. After removal of the supernatant, the particles were resuspended in 10 ml of distilled water, and the resulting suspension was subjected to centrifugation under the same conditions as described above to perform reprecipitation of the particles. This operation of washing was repeated once more and, after removal of the supernatant, the particles were suspended in 200 µl of an aqueous solution containing 5% (w/v) mannitol, 0.5% (w/v) sodium carboxymethylcellulose and 0.1% (w/v) polysorbate 80. The resulting suspension was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours, to obtain an immunogenic microparticle.

As a surfactant, polysorbate 80, polysorbate 20, sorbitan trioleate or sorbitan monooleate (these were manufactured by Kanto Chemical Co., Inc.) or polyoxyethylene hydrogenated castor oil (manufactured by Nikko Chemicals Co., Ltd.) was dissolved in the aqueous CEA solution (A), amphiphilic polymer solution (B) or dispersion (C) as shown in Table 1, in an amount of 500 µg, which corresponded to 10% (w/w) with respect to the amount of the amphiphilic polymer.

TABLE 1

Method of preparing immunogenic microparticles (Particles (1) to (10) and Comparative Particles (1) and (2))

| Particle No. | Solution to which surfactant was added | Type of surfactant | Type of surface modifier |
|---|---|---|---|
| Particle (1) | Dispersion (C) | Polysorbate 80 | Polyvinyl alcohol |
| Particle (2) | Dispersion (C) | Sorbitan trioleate | Polyvinyl alcohol |
| Particle (3) | Dispersion (C) | Polysorbate 80 | Pluronic F68 |

TABLE 1-continued

Method of preparing immunogenic microparticles (Particles (1) to (10) and Comparative Particles (1) and (2))

| Particle No. | Solution to which surfactant was added | Type of surfactant | Type of surface modifier |
|---|---|---|---|
| Particle (4) | Dispersion (C) | Sorbitan trioleate | Pluronic F68 |
| Particle (5) | Dispersion (C) | Polysorbate 20 | Pluronic F68 |
| Particle (6) | Dispersion (C) | Sorbitan monooleate | Pluronic F68 |
| Particle (7) | Dispersion (C) | Polyoxyethylene hydrogenated castor oil | Pluronic F68 |
| Particle (8) | Aqueous CEA solution (A) | Polysorbate 80 | Pluronic F68 |
| Particle (9) | Amphiphilic polymer solution (B) | Polysorbate 80 | Pluronic F68 |
| Particle (10) | Dispersion (C) | Polysorbate 80 | Pluronic F68 |
| Comparative Particle (1) | — | — | Polyvinyl alcohol |
| Comparative Particle (2) | — | — | Pluronic F68 |

Example 3 Measurement of Antigen Encapsulation Rate in Immunogenic Microparticle Method Each type of immunogenic microparticles prepared by the method in Example 2 (Particles (3) to (7) and Comparative Particle (2)) was dissolved in 200 μl of phosphate-buffered physiological saline, to prepare a particle suspension. In an Eppendorf tube, 100 μl of the particle suspension was placed, and 1 ml of distilled water was added thereto, followed by centrifuging the resulting mixture at 13,000 rpm for 10 minutes to precipitate the particles. After removal of the supernatant, the particles were resuspended in 1 ml of distilled water, and the resulting suspension was subjected to centrifugation under the same conditions as described above to perform reprecipitation of the particles. After removal of the supernatant, the particles were dissolved in 0.5 ml of a 1:3 mixed solution of methylene chloride and acetone. The resulting particle solution was subjected to centrifugation at 13,000 rpm for 10 minutes, to precipitate CEA. After removal of the supernatant, the precipitate was dissolved in 0.5 ml of the mixed solution, and centrifugation was carried out under the above-described conditions to reprecipitate CEA. After removal of the supernatant, centrifugal drying was carried out for 30 minutes for drying the CEA precipitate. A sampling buffer for gel electrophoresis (manufactured by TEFCO) was added to the CEA precipitate, and the precipitate was dissolved therein at 95° C. for 3 minutes, followed by performing gel electrophoresis using polyacrylamide gel (manufactured by TEFCO). Thereafter, the gel was stained using colloidal CBB staining kit (manufactured by TEFCO), and the rate of encapsulation of CEA into the particles was calculated. The results are shown in Table 2.

Results

The antigen (CEA) encapsulation rates of the immunogenic microparticles were as shown in Table 2, and it was shown that the encapsulation rate was almost the same between any of the immunogenic microparticles containing a surfactant (Particles (3) to (7)) and the particle containing no surfactant (Comparative Particle (2)). Thus, it was shown that the surfactants do not adversely affect the antigen encapsulation rate of the immunogenic microparticle.

TABLE 2

Encapsulation rate of CEA in immunogenic microparticles (Particles (3) to (7) and Comparative Particle (2))

| Particle No. | Type of surfactant | Encapsulation rate of CEA |
|---|---|---|
| Particle (3) | Polysorbate 80 | 65% |
| Particle (4) | Sorbitan trioleate | 46% |
| Particle (5) | Polysorbate 20 | 62% |
| Particle (6) | Sorbitan monooleate | 71% |
| Particle (7) | Polyoxyethylene hydrogenated castor oil | 66% |
| Comparative Particle (2) | — | 55% |

Example 4 Subcutaneous Administration of CEA-containing Immunogenic Composition to Mice (1)

Method

Each type of the immunogenic microparticles prepared in Example 2 containing polysorbate 80 or sorbitan trioleate (Particles (1) and (2)) was suspended in 200 μl of phosphate-buffered physiological saline, to provide an administration solution. This solution was subcutaneously administered by single injection to the back of male Balb/C mice of 7 weeks old (Japan SLC, Inc.) at a dose of 5 μg in terms of CEA per individual. As Comparative Examples, particles containing no surfactant (Comparative Particle (1)) or a solution prepared by mixing 50 μl of the CEA solution with 50 μl of "Imject Alum" (manufactured by Thermo Scientific, hereinafter also referred to as Alum) as an adjuvant was subcutaneously administered by single injection to the back of male Balb/C mice at a dose of 5 μg in terms of CEA per individual. Under each condition, the administration was carried out for 5 individuals of mice. Changes in the antibody titer with time are shown in FIG. 1.

The mice after the administration were kept in an environment in which the mice can freely take food and water, while blood was collected from the tail vein with time. To the collected blood, heparin was added to a final concentration of 3.3 IU/ml, and centrifugation was carried out at 5,000 rpm for 5 minutes to collect blood plasma, followed by measuring the antibody titer against CEA in the blood plasma. The antibody titer against CEA was measured by the following method. In a 96-well microplate (MaxiSorp, manufactured by Nunc), 100 μl of a PBS solution containing 1 μg/ml CEA protein was placed, and the plate was left to stand at 4° C. overnight. The solution was discarded, and 400 μl of PBS supplemented with 0.5% BSA was placed in the plate, followed by carrying out blocking at room temperature for 2 hours. The well was washed once with 400 µl of a washing liquid (PBS supplemented with 0.05% Tween 20), and 100 µl of a blood plasma sample which had been 1,000- to 100,000-fold diluted with a dilution liquid (PBS supplemented with 0.25% BSA and 0.05% Tween 20) was placed in the well, followed by allowing the reaction to proceed at room temperature for 40 minutes with shaking. The well was washed three times with the washing liquid, and 100 µl of HRP (horse radish peroxidase)-labeled anti-mouse IgG antibody (Zymed) (10,000-fold diluted with the dilution liquid) was placed in the well, followed by allowing the reaction to proceed at room temperature for 20 minutes with shaking. The well was washed three times with the washing liquid, and 100 µl of a coloring liquid (0.1 M sodium acetate/citrate buffer (pH 4.5) containing 0.006% hydrogen peroxide and 0.2 mg/ml tetramethylbenzidine) was placed in the well, followed by allowing the reaction to proceed at room temperature for 10 minutes with shaking The reaction was stopped by addition of 100 µl of 1 N sulfuric acid, and the absorbance at 450 nm was measured using a microplate reader. As a standard sample, a serially diluted anti-CEA monoclonal antibody (MA1-5308, manufactured by Affinity Bioreagents) was measured at the same time to provide a calibration curve, and the amount of antibody in each sample was calculated in terms of concentration by weight (ng/ml).

Results

Changes in the mean value of the anti-CEA antibody titer in blood plasma with time are shown in FIG. 1. The Particle (1) containing polysorbate 80 and the Particle (2) containing sorbitan trioleate showed a continuous effect of increasing the antibody titer for 8 weeks, and the effect was much higher than in Comparative Example wherein the antigen+ Alum was administered. The antibody titer was even higher than in Comparative Particle (1) containing no surfactant, and it was shown that the immunogenic microparticle shows a higher adjuvant capacity by inclusion of a surfactant.

Example 5 Subcutaneous Administration of CEA-Containing Immunogenic Composition to Mice (2)

Method

Figure 2:
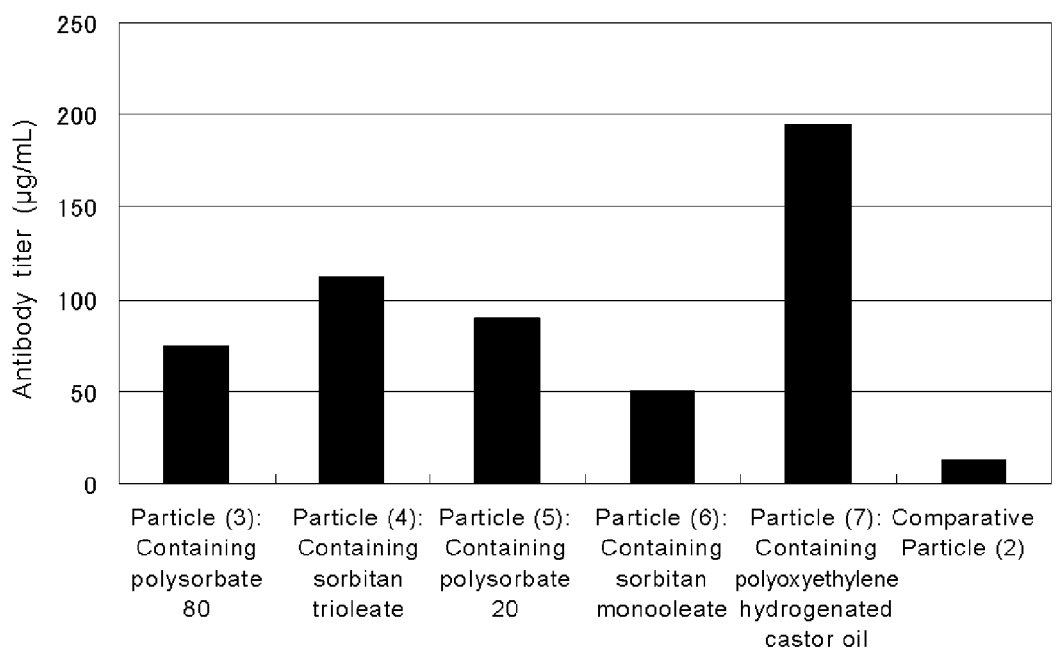
FIG. 2 shows immunological evaluation 2 of CEA-containing immunogenic microparticles.

Each type of the immunogenic microparticles prepared in Example 2 (Particles (3) to (7)) was subcutaneously administered by single injection to the back of male Balb/C mice of 7 weeks old (Japan SLC, Inc.) at a dose of 5 µg in terms of CEA per individual by the method described in Example 4. As Comparative Example, particles containing no surfactant (Comparative Particle (2)) were subcutaneously administered by single injection to the back of male Balb/C mice at a dose of 5 µg in terms of CEA per individual. Under each condition, the administration was carried out for 5 individuals of mice. FIG. 2 shows the mean value of the antibody titer. Collection of blood and measurement of the antibody titer were carried out by the methods described in Example 4.

Results

The mean value of the anti-CEA antibody titer in blood plasma at Week 4 after the administration is shown in FIG. 2. Similarly to the cases of particles containing polysorbate 80 or sorbitan trioleate ((3), (4)) described in Example 4, the particles containing polysorbate 20, sorbitan monooleate or polyoxyethylene hydrogenated castor oil ((5) to (7)) also showed higher values of the antibody titer compared to Comparative Particle (2) containing no surfactant. Thus, it was shown that the immunogenic microparticle shows a higher adjuvant capacity by inclusion of a surfactant.

Example 6 Subcutaneous Administration of CEA-Containing Immunogenic Composition to Mice (3)

Method

Figure 3:
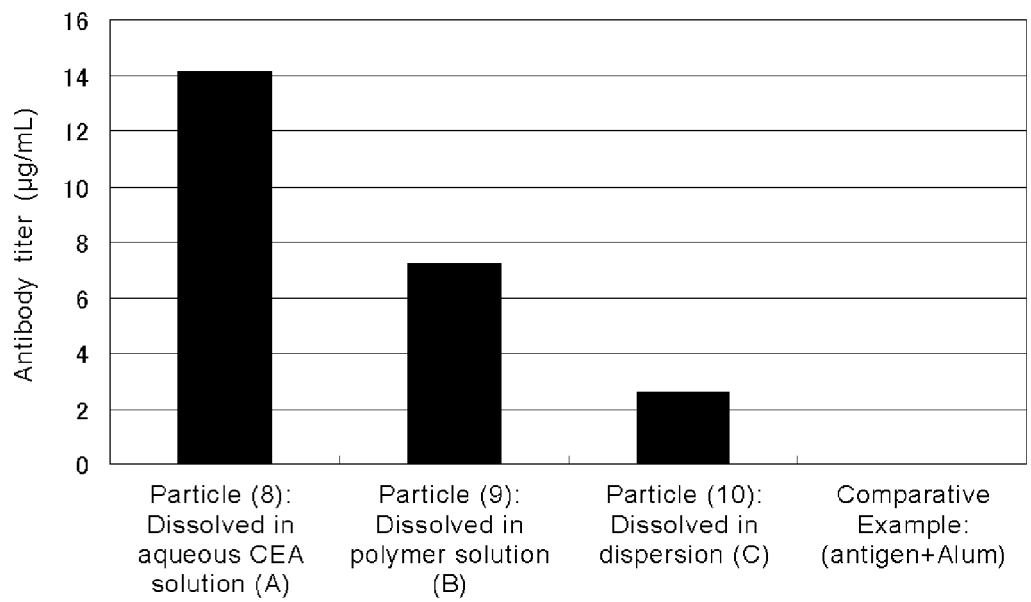
FIG. 3 shows immunological evaluation 3 of CEA-containing immunogenic microparticles.

Each type of the immunogenic microparticles prepared in Example 2 containing polysorbate 80 (Particles (8) to (10)) was administered by single injection to the footpad of male Balb/C mice of 7 weeks old (Japan SLC, Inc.) at a dose of 5 µg in terms of CEA per individual by the method described in Example 4. As Comparative Example, a solution was prepared by mixing 50 µl of the antigen solution and 50 µl of Alum, and the resulting mixture was administered by single injection to the footpad of male Balb/C mice at a dose of 5 µg in terms of CEA per individual. Under each condition, the administration was carried out for 3 individuals of mice. FIG. 3 shows the mean value of the antibody titer. Measurement of the antibody titer was carried out by the method described in Example 4.

Results

The mean value of the anti-CEA antibody titer in blood plasma at Week 2 after the administration is shown in FIG. 3. In all types of particles ((8) to (10)) in which different solutions were used for dissolving polysorbate 80 in the preparation process, the antibody titer was drastically higher than in administration of the antigen+Alum in Comparative Example. That is, it was shown that the immunogenic microparticle has a strong adjuvant capacity also when the surfactant was dissolved in any of the aqueous CEA solution (A), amphiphilic polymer solution (B) and dispersion (C).

Example 7 Measurement of Surfactant Contained in Immunogenic Microparticle Method The immunogenic microparticles (Particle (1)) containing polysorbate 80 prepared in Example 2 were suspended in 1 ml of distilled water, and precipitated by centrifugation at 13,000 rpm for 10 minutes. After removal of the supernatant, the particles were resuspended in 1 ml of distilled water, and subjected to centrifugation under the same conditions as described above to reprecipitate the particles. After removal of the supernatant, the particles were dissolved in 100 µl of ethyl acetate. To this particle solution, 300 µl of ethanol was added, and the resulting mixture was subjected to centrifugation at 13,000 rpm for 10 minutes to precipitate the amphiphilic polymer. The supernatant was collected and the solvent was removed by evaporation under reduced pressure, followed by dissolving the residue in 100 µl of distilled water, to prepare a particle extract. The particle extract was analyzed by high performance liquid chromatography (manufactured by Shimadzu Corporation) using a reverse-phase column (YMC-Pack PROTEIN-RP, manufactured by YMC), to measure the content of polysorbate 80 contained in the immunogenic microparticle.

Results

By the analysis by high performance liquid chromatography, it was found that the particle extract contained 0.24% (w/v) polysorbate 80. Based on this result, it was revealed that the immunogenic microparticle contains polysorbate 80 in an amount of 4.8% (w/w) with respect to the fed amount of the amphiphilic polymer constituting the immunogenic microparticle, and it was shown that 48% (w/w) of the polysorbate 80 added in the preparation process in Example 2 was contained in the immunogenic microparticle.

Example 8 Preparation of CEA-Containing Immunogenic Microparticles (Particles (11) to (15) and Comparative Particles (3) to (5))

In 100 µl of dimethyl carbonate, 5 mg of the dextran-poly(lactic-co-glycolic acid) (PLGA) (Compound (2)) prepared in Example 1 was dissolved, to prepare a 50 mg/ml amphiphilic polymer solution (B). To the amphiphilic polymer solution (B), 20 µl of tert-butanol was added, and 50 µl of 0.025% (w/v) aqueous CEA (carcinoembryonic antigen) (COSMO BIO Co., Ltd.) solution (A) was added dropwise thereto, followed by stirring the resulting mixture with a vortex mixer to produce a reversed-phase emulsion.

The reversed-phase emulsion was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours. The obtained solids were dispersed in 200 µl of dimethyl carbonate, to prepare a dispersion (C). The dispersion (C) was added dropwise to 2 ml of an aqueous solution (D) containing 10% (w/v) surface modifier (Pluronic F-68), and the resulting mixture was stirred and emulsified with a vortex mixer, to prepare an S/O/W emulsion. From the S/O/W emulsion, dimethyl carbonate was removed by solvent evaporation, to prepare an immunogenic microparticle suspension. The suspension was transferred to a 15-ml tube, and subjected to centrifugation at 8,000 rpm for 10 minutes, to precipitate the particles. After removal of the supernatant, the particles were resuspended in 10 ml of distilled water, and the resulting suspension was subjected to centrifugation under the same conditions as described above to perform reprecipitation of the particles. This operation of washing was repeated once more and, after removal of the supernatant, the particles were suspended in 200 µl of an aqueous solution (Injection Solution (E)) containing 5% (w/v) mannitol, 0.5% (w/v) sodium carboxymethylcellulose and 0.1% (w/v) polysorbate 80. The resulting suspension was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours, to obtain an immunogenic microparticle.

As a surfactant, polysorbate 80 was dissolved in the aqueous CEA solution (A), amphiphilic polymer solution (B) or dispersion (C) as shown in Table 3, in an amount corresponding to 10% (w/w), 1% (w/w) or 0.1% (w/w) with respect to the amount of the amphiphilic polymer, to prepare particles (11) to (15). Further, in terms of Comparative Particles, polysorbate 80 was dissolved in the aqueous solution (D) containing a surface modifier or injection solution (E), in the amount corresponding to 10% (w/w) with respect to the amount of the amphiphilic polymer, to prepare Comparative Particle (3) in which the surfactant is bound to the surfaces of microparticles, Comparative Particle (4) in which the surfactant and immunogenic microparticles coexist without being bound to each other, as well as Comparative Particle (5) in which the surfactant was not added in the process of preparation of immunogenic microparticles.

TABLE 3

Method of preparing CEA-containing immunogenic microparticles (Particles (11) to (15) and Comparative Particles (3) to (5))

| Particle No. | Solution to which surfactant was added | Amount of surfactant added |
|---|---|---|
| Particle (11) | Aqueous CEA solution (A) | 10% (w/w) |
| Particle (12) | Amphiphilic polymer solution (B) | 10% (w/w) |
| Particle (13) | Dispersion (C) | 10% (w/w) |
| Particle (14) | Aqueous CEA solution (A) | 1% (w/w) |
| Particle (15) | Aqueous CEA solution (A) | 0.1% (w/w) |
| Comparative Particle (3) | Aqueous solution (D) containing surface modifier | 10% (w/w) |
| Comparative Particle (4) | Injection solution (E) | 10% (w/w) |
| Comparative Particle (5) | — | — |

Example 9 Subcutaneous Administration of CEA-Containing Immunogenic Composition to Mice (4)

Method

Figure 4:
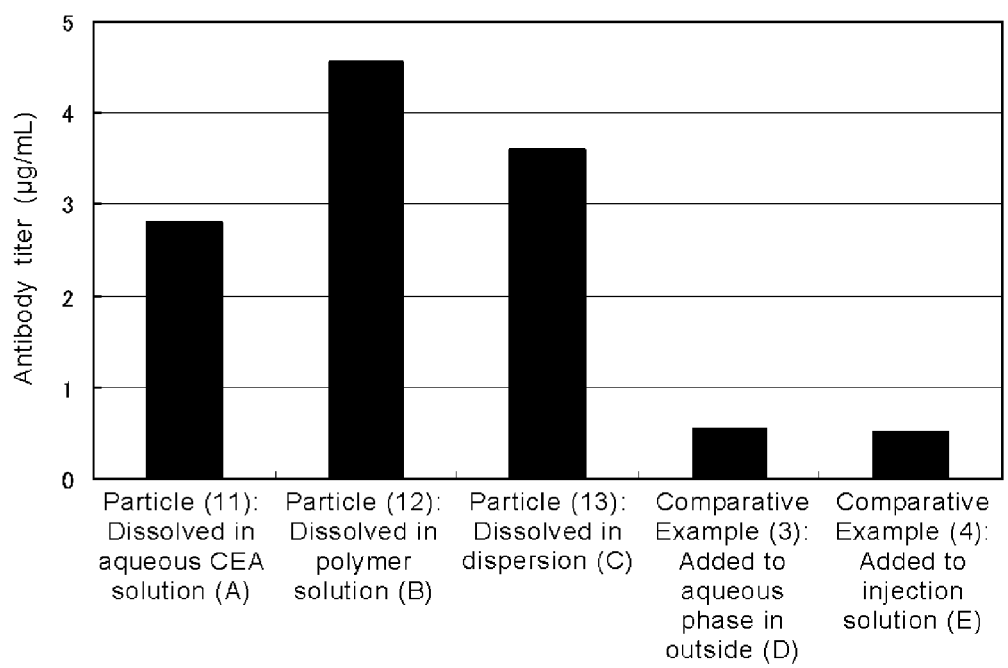
FIG. 4 shows immunological evaluation 4 of CEA-containing immunogenic microparticles.

Each type of the immunogenic microparticles prepared in Example 8 (Particles (11) to (13)) was subcutaneously administered by the method described in Example 4 by single injection to the back of male Balb/C mice of 7 weeks old (Japan SLC, Inc.) at a dose of 5 µg in terms of CEA per individual. As Comparative Examples, particles to which the surfactant was added in different manners (Comparative Particles (3) and (4)) were subcutaneously administered by single injection to the back of Balb/C mice at a dose of 5 µg in terms of CEA per individual. Under each condition, the administration was carried out for 5 individuals of mice. FIG. 4 shows the mean value of the antibody titer. Collection of blood and measurement of the antibody titer were carried out by the methods described in Example 4.

Results

The mean value of the anti-CEA antibody titer in blood plasma at Week 5 after the administration is shown in FIG. 4. In the cases where the surfactant was added to the aqueous CEA solution (A), polymer solution (B) or dispersion (C) (Particles (11) to (13)), the surfactant is present inside the S/O/W emulsion so that the surfactant is encapsulated in the microparticle. On the other hand, in the particle (Comparative Particle (3)) added to the aqueous solution (D) containing a surface modifier, polysorbate 80 is present outside the S/O/W emulsion so that the surfactant is bound to the surface of the microparticle. In the particle (Comparative Particle (4)) added to the injection solution (E), the surfactant and the microparticles coexist without being bound to each other. Since the immunogenic microparticles (Particles (11) to (13)) wherein the surfactant is encapsulated showed higher antibody titers compared to the particle (Comparative Particles (3)) wherein the surfactant is bound to the surface and the particle (Comparative Particles (4)) wherein the surfactant is not bound to the surface, it was shown that encapsulation of the surfactant in the immunogenic microparticle is important.

Example 10 Subcutaneous Administration of CEA-Containing Immunogenic Composition to Mice (5)

Method

Figure 5:
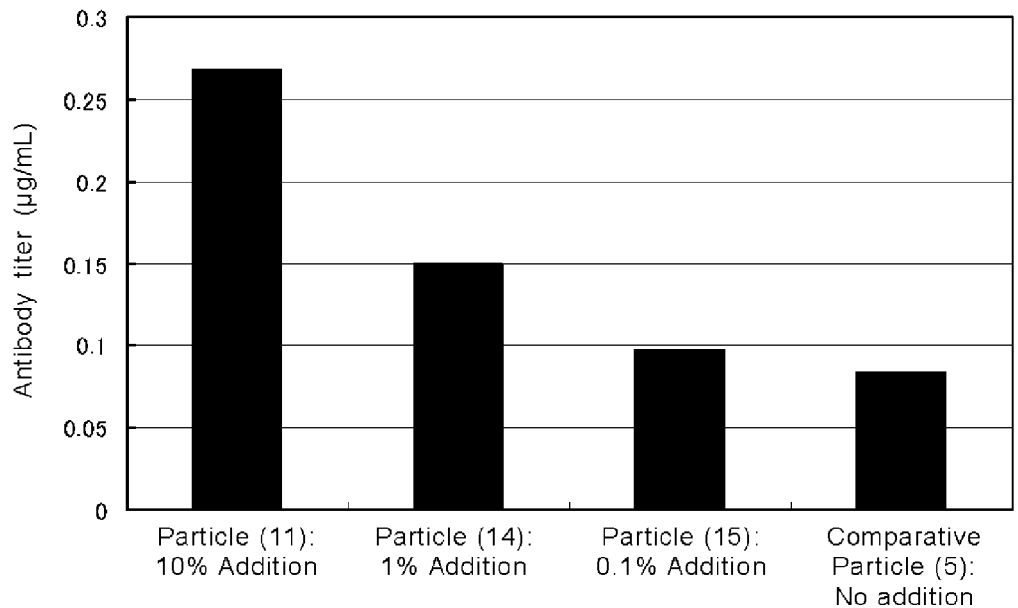
FIG. 5 shows immunological evaluation 5 of CEA-containing immunogenic microparticles.

Each type of the immunogenic microparticles prepared in Example 8 (Particles (11), (14) and (15)) was subcutaneously administered by the method described in Example 4 by single injection to the back of male Balb/C mice of 7 weeks old (Japan SLC, Inc.) at a dose of 5 µg in terms of CEA per individual. As Comparative Example, particles containing no surfactant (Comparative Particle (5)) were subcutaneously administered by single injection to the back of Balb/C mice at a dose of 5 µg in terms of CEA per individual. Under each condition, the administration was carried out for 5 individuals of mice. FIG. 5 shows the mean value of the antibody titer. Collection of blood and measurement of the antibody titer were carried out by the methods described in Example 4.

Results

The mean value of the anti-CEA antibody titer in blood plasma at Week 3 after the administration is shown in FIG. 5. The particles wherein a surfactant is encapsulated (Particles (11), (14) and (15)) showed higher antibody titers compared to the particle containing no surfactant (Comparative Particle (5)). Further, among the particles wherein a surfactant is encapsulated, the more the amount of the surfactant added, the higher the antibody titer. Thus, it was shown that the effect increases as the amount of the surfactant encapsulated in the particle increases.

Example 11 Measurement of Surfactant Contained in Immunogenic Microparticle (2)

Method

The immunogenic microparticles prepared in Example 8 (Particles (11) to (13) and Comparative Particle (3)) were used to measure the contents of polysorbate 80 contained in the immunogenic microparticles, by the method described in Example 7.

Results

By high performance liquid chromatography, the content of polysorbate 80 with respect to the fed amount of the amphiphilic polymer constituting the immunogenic microparticle or with respect to the amount of the surfactant fed in the production process was analyzed. The results are shown in Table 4. In the particles wherein a surfactant was added to the aqueous CEA solution (A), amphiphilic polymer solution (B) or dispersion (C) (Particles (11) to (13)), the surfactant was encapsulated in the microparticles in the preparation process. Accordingly, it was shown that about 30% (w/w) of the surfactant added in the preparation process in Example 8 was contained in the particles. On the other hand, in the particles (Comparative Particle (3)) prepared by the process wherein the surfactant was added to the aqueous solution (D) containing a surface modifier, the surfactant is bound to the surfaces of the microparticles, and it was shown that only about 3% of the surfactant added in the preparation process was contained.

TABLE 4

Amount of the surfactant contained in immunogenic microparticles (Particles (11) to (13) and Comparative Particle (3))

| Particle No. | Content of surfactant with respect to amphiphilic polymer | Content of surfactant with respect to the amount added |
| --- | --- | --- |
| Particle (11) | 3.90 (w/w) % | 39.0 (w/w) % |
| Particle (12) | 3.03 (w/w) % | 30.3 (w/w) % |
| Particle (13) | 2.89 (w/w) % | 28.9 (w/w) % |
| Comparative Particle (3) | 0.23 (w/w) % | 2.3 (w/w) % |

Example 12 Preparation of OVA-Containing Immunogenic Microparticles (Particles (16) to (18) and Comparative Particle (6))

In 100 µl of dimethyl carbonate, 5 mg of the dextran-poly(lactic-co-glycolic acid) (PLGA) (Compound (2)) prepared in Example 1 was dissolved, to prepare a 50 mg/ml amphiphilic polymer solution (B). To the amphiphilic polymer solution (B), 20 µl of tert-butanol was added, and 50 µl of 0.25% (w/v) aqueous OVA (ovalbumin) (SIGMA) solution (A) was then added dropwise thereto (amount of OVA fed, 125 µg), followed by stirring the resulting mixture with a vortex mixer to produce a reversed-phase emulsion.

The reversed-phase emulsion was subjected to prior freezing with liquid nitrogen, and freeze-dried using a freeze dryer (EYELA, FREEZE DRYER FD-1000) at a trap cooling temperature of −45° C. at a degree of vacuum of 20 Pa for 24 hours. The obtained solids were dispersed in 200 µl of dimethyl carbonate, to prepare a dispersion. The dispersion was added dropwise to 2 ml of an aqueous solution (C) containing 10% (w/v) surface modifier (Pluronic F-68), and the resulting mixture was stirred and emulsified with a vortex mixer, to prepare an S/O/W emulsion. From the S/O/W emulsion, dimethyl carbonate was removed by solvent evaporation, to prepare an immunogenic microparticle suspension. The suspension was transferred to an eggplant type flask, and subjected to prior freezing with liquid nitrogen, followed by freeze-drying using a freeze dryer (EYELA, FREEZE DRYER FD-1000) at a trap cooling temperature of −45° C. at a degree of vacuum of 20 Pa for 24 hours, to obtain immunogenic microparticles.

As shown in Table 5, in terms of the surfactant, polysorbate 80 or sorbitan monooleate (these were manufactured by Kanto Chemical Co., Inc.) or polyoxyethylene hydrogenated castor oil (manufactured by Nikko Chemicals Co., Ltd.) was dissolved in the aqueous OVA solution (A) or amphiphilic polymer solution (B), in an amount of 500 µg, which corresponded to 10% (w/w) with respect to the amount of the amphiphilic polymer.

TABLE 5

Method of preparing OVA-containing immunogenic microparticles (Particles (16) to (18) and Comparative Particle (6))

| Particle No. | Solution to which surfactant was added | Type of surfactant |
| --- | --- | --- |
| Particle (16) | Aqueous CEA solution (A) | Polysorbate 80 |
| Particle (17) | Amphiphilic polymer solution (B) | Sorbitan monooleate |
| Particle (18) | Aqueous CEA solution (A) | Polyoxyethylene hydrogenated castor oil |
| Comparative Particle (6) | — | — |

Example 13 In Vitro Stimulation Test of OVA-Containing Immunogenic Compositions Using Mouse Peritoneal Macrophages Method An in vitro stimulation test using mouse peritoneal macrophages was carried out by the following method. Using a 26-G injection needle (Terumo Corporation), 5 ml of thioglycollate medium (GIBCO) as a stimulation liquid was intraperitoneally administered to a male Balb/c mouse of 12 weeks old, and the mouse was kept for 72 hours in an environment in which the mouse can freely take food. The mouse was then euthanized using dry ice, and 10 ml of PBS solution (0° C., filtered) was intraperitoneally injected to the mouse using a 26-G injection needle, followed by leaving the mouse to stand while massaging the abdomen of the mouse for 5 minutes. Thereafter, a solution containing abdominal cells was collected using a micropipette.

The collected solution was centrifuged using a refrigerated centrifuge (manufactured by Hitachi, Ltd., himacCF16RX) at 4° C. at 400 g×5 minutes to precipitate the mouse abdominal cells, and the supernatant was removed, followed by adding 10 ml of RPMI1640 medium (GIBCO) (hereinafter referred to as washing solution) thereto and resuspending the cells. Centrifugation was carried out again at 400 g×5 minutes at 4° C. to remove the supernatant, and the cells were plated in a 24-well plate (microplate manufactured by Iwaki, Flat Bottom Tissue culture Treated, Polystyrene) such that each well contained $8\times10^5$ cells together with 1 ml of RPMI1640 medium supplemented with 5% FBS (SIGMA), 100 U/ml penicillin (Invitrogen) and 100 U/ml streptomycin (Invitrogen) (hereinafter referred to as culture medium). The plate after plating was incubated using a $CO_2$ incubator (NAPCO) under 5% $CO_2$ at 37° C. at 100% humidity (conditions for macrophage culture) for 3 hours, and the cells were vigorously suspended using a micropipette to remove cells that did not adhere to the plate, to obtain only mouse peritoneal macrophages adhering to the plate. The culture medium was added to the cells, and the cells were incubated under the culture conditions for macrophages for 5 days, to provide cells to be used in the experiment.

As the particles to be added to the cells, the immunogenic microparticles (Particles (16) to (18)) prepared in Example 12 wherein the surfactant is encapsulated, which microparticles were in the freeze-dried state, were used after pretreatment. More specifically, particles in the amount corresponding to 3 mg in terms of the amount of the amphiphilic polymer constituting the particles were weighed and placed in a 1.5-ml tube. The washing solution was added thereto, and the resulting mixture was precooled to 0° C., followed by washing the particles 3 times at 8400 g for 10 minutes. Thereafter, the particles were added to the 24-well plate wherein the mouse peritoneal macrophages were plated, together with 500 µl/well of the culture medium. As Comparative Example, particles containing no surfactant (Comparative Particle (6)) were similarly added.

Further, as shown in Table 6 as other Comparative Examples (Comparative Examples (1) to (3)), OVA in an amount of 75 µg (calculated based on the weight ratio between the fed amount of the amphiphilic polymer and the fed amount of OVA), which was the same as the amount of OVA contained in Particles (16) to (18), and 300 µg of polysorbate 80, sorbitan monooleate or polyoxyethylene hydrogenated castor oil were added to each well of the 24-well plate wherein the mouse peritoneal macrophages were plated, together with 500 µl of the culture medium. Further, as Comparative Example (4), 75 µg of OVA was added together with 500 µl of the culture medium.

TABLE 6

Types and amounts of surfactants added in in vitro stimulation tests in Comparative Examples (Comparative Examples (1) to (4))

| Comparative Examples | Type of surfactant | Amount of surfactant added |
|---|---|---|
| Comparative Example (1) | Polysorbate 80 | 300 µg |
| Comparative Example (2) | Sorbitan monooleate | 300 µg |
| Comparative Example (3) | Polyoxyethylene hydrogenated castor oil | 300 µg |
| Comparative Example (4) | — | — |

The cells to which the particles were added were cultured for 24 hours, and the medium was recovered, followed by measuring the amount of TNFα contained in the medium with ELISA. The measurement with ELISA was carried out using a kit manufactured by Thermo Scientific.

Results

Figure 6:
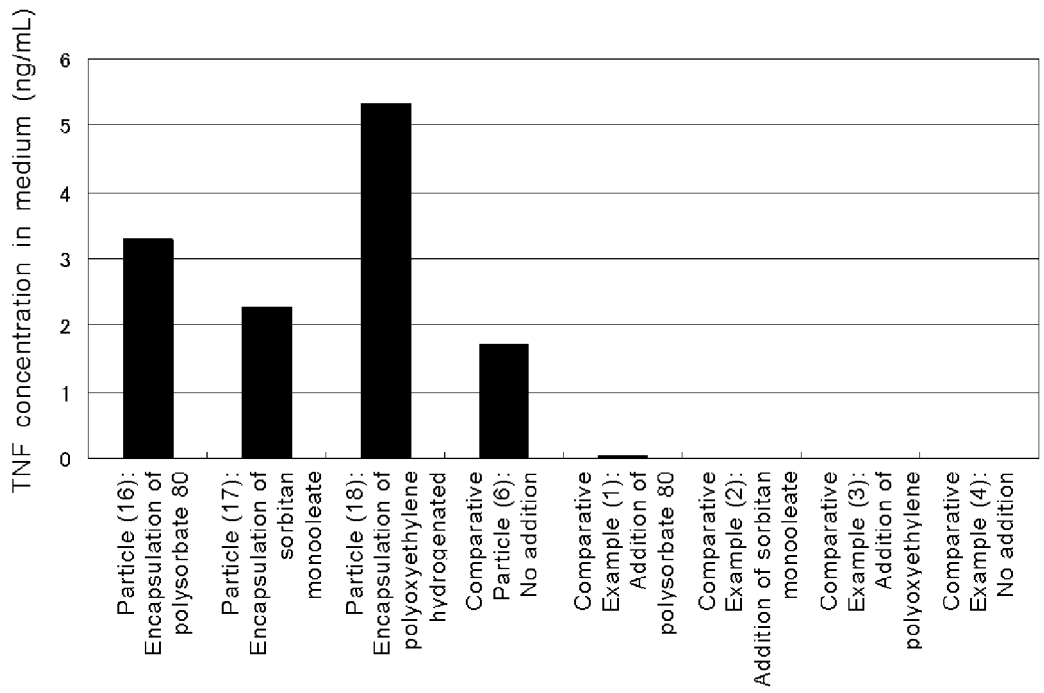
FIG. 6 shows immunological evaluation of OVA-containing immunogenic microparticles.

The concentration of TNFα in the medium was as shown in FIG. 6. The particles wherein a surfactant is encapsulated (Particles (16) to (18)) showed higher TNFα concentrations compared to the particles (Comparative Particle (6)) wherein no surfactant is encapsulated. TNFα is a kind of cytokine that induces immunity, and it was shown that efficient induction of immunity can be achieved by encapsulation of a surfactant in the particle. Further, in the Comparative Examples wherein the antigen was not in the form of particles and was added together with a surfactant (Comparative Examples (1) to (4)), the TNFα concentration was lower than in the cases where the antigen was in the form of particles. Thus, it was shown that formation into particles is important for induction of immunity.

INDUSTRIAL APPLICABILITY

The immunogenic composition can be used as a vaccine for therapy and/or prophylaxis of infectious diseases, cancers and the like.

The invention claimed is:
1. A process of producing an immunogenic particle comprising:
  mixing an aqueous solvent A wherein an antigen(s) is/are dissolved and a water-immiscible organic solvent B wherein an amphiphilic polymer(s) whose hydrophobic segment(s) is/are poly(hydroxy acid) is/are dissolved, to form a reversed-phase emulsion; and
  removing the solvent from said reversed-phase emulsion to obtain an antigen-adjuvant microparticle complex, wherein said
  aqueous solvent A and/or said water-immiscible organic solvent B contains a nonionic surfactant such that immunogenicity of said antigen is enhanced by said nonionic surfactant encapsulated in said microparticle.
2. A process of producing an immunogenic particle comprising:
  mixing an aqueous solvent A wherein an antigen(s) is/are dissolved and a water-immiscible organic solvent B wherein an amphiphilic polymer(s) whose hydrophobic segment(s) is/are poly(hydroxy acid) is/are dissolved, to form a reversed-phase emulsion;
  removing the solvent from said reversed-phase emulsion to obtain an antigen-adjuvant microparticle complex; and
  introducing an antigen-adjuvant microparticle complex dispersion C to a liquid phase D wherein a surface modifier is dissolved, followed by removing the dispersion medium, wherein said aqueous solvent A, said water-immiscible organic solvent B and/or said dispersion C contains a nonionic surfactant such that immunogenicity of said antigen is enhanced by said nonionic surfactant encapsulated in said microparticle.

3. The process according to claim 1, wherein said nonionic surfactant comprises a fatty acid ester structure.

4. The process according to claim 1, wherein said hydrophilic segment of said amphiphilic polymer is a polysaccharide.

5. The process according to claim 1, wherein said amphiphilic polymer is a graft amphiphilic polymer composed of a polysaccharide backbone and a poly(hydroxy acid) graft chain(s).

6. The process according to claim 4, wherein said polysaccharide is dextran.

7. The process according to claim 4, wherein said poly(hydroxy acid) is poly(lactic-co-glycolic acid).

8. The process according to claim 1, wherein said nonionic surfactant further comprises a monosaccharide and/or polyethylene glycol structure(s).

9. The process according to claim 1, wherein said nonionic surfactant is one or more selected from the group consisting of polysorbate 80, polysorbate 20, sorbitan monooleate, sorbitan trioleate and polyoxyethylene hydrogenated castor oil.

10. The process according to claim 1, wherein said nonionic surfactant(s) is contained in said aqueous solvent A and/or said water-immiscible organic solvent B in an amount of 0.01 to 50% (w/w) based on the amount of the amphiphilic polymer(s) dissolved in said water-immiscible organic solvent B.

11. The process according to claim 1, wherein said nonionic surfactant(s) is contained in said aqueous solvent A, said water-immiscible organic solvent B and/or said dispersion C in an amount of 0.01 to 50% (w/w) based on the amount of the amphiphilic polymer(s) dissolved in said water-immiscible organic solvent B.

12. The process according to claim 2, wherein said nonionic surfactant comprises a fatty acid ester structure.

13. The process according to claim 2, wherein said hydrophilic segment of said amphiphilic polymer is a polysaccharide.

14. The process according to claim 2, wherein said amphiphilic polymer is a graft amphiphilic polymer composed of a polysaccharide backbone and a poly(hydroxy acid) graft chain(s).

15. The process according to claim 13, wherein said polysaccharide is dextran.

16. The process according to claim 13, wherein said poly(hydroxy acid) is poly(lactic-co-glycolic acid).

17. The process according to claim 2, wherein said nonionic surfactant further comprises a monosaccharide and/or polyethylene glycol structure(s).

18. The process according to claim 2, wherein said nonionic surfactant is one or more selected from the group consisting of polysorbate 80, polysorbate 20, sorbitan monooleate, sorbitan trioleate and polyoxyethylene hydrogenated castor oil.

* * * * *